US008968704B2

(12) United States Patent
Sato et al.

(10) Patent No.: US 8,968,704 B2

(45) Date of Patent: Mar. 3, 2015

(54) FLUORESCENT LABELING MATERIAL AND FLUORESCENT LABELING AGENT

(75) Inventors: Moriyuki Sato, Matsue (JP); Morihiko Nakamura, Izumo (JP)

(73) Assignee: National University Corporation Shimane University, Shimane (JP)

( * ) Notice: Subject to any disclaimer, the term of this patent is extended or adjusted under 35 U.S.C. 154(b) by 674 days.

(21) Appl. No.: 13/064,979

(22) Filed: Apr. 29, 2011

(65) Prior Publication Data

US 2011/0206618 A1 Aug. 25, 2011

Related U.S. Application Data

(63) Continuation of application No. PCT/JP2009/067643, filed on Oct. 9, 2009.

(30) Foreign Application Priority Data

Oct. 30, 2008 (JP) ................................ 2008-279248

(51) Int. Cl.

| | |
|---|---|
| ***A61B 5/00*** | (2006.01) |
| ***A61K 9/00*** | (2006.01) |
| ***H01L 31/101*** | (2006.01) |
| ***C12Q 1/68*** | (2006.01) |
| ***B32B 5/16*** | (2006.01) |
| ***C09K 11/54*** | (2006.01) |
| ***A61K 49/00*** | (2006.01) |
| ***C09K 11/02*** | (2006.01) |
| ***G01N 33/58*** | (2006.01) |

(52) U.S. Cl.

CPC ............. *C09K 11/54* (2013.01); *A61K 49/0017* (2013.01); *A61K 49/0054* (2013.01); *A61K 49/0067* (2013.01); *A61K 49/0093* (2013.01); *C09K 11/025* (2013.01); *G01N 33/582* (2013.01); *G01N 33/587* (2013.01)

USPC ........... 424/9.6; 424/400; 257/114; 435/6.11; 428/403

(58) Field of Classification Search

None

See application file for complete search history.

(56) References Cited

U.S. PATENT DOCUMENTS

| | | | | |
|---|---|---|---|---|
| 2004/0180823 A1* | 9/2004 | Pasquale et al. | ................ | 514/12 |
| 2006/0086925 A1 | 4/2006 | Hirai et al. | | |
| 2008/0020483 A1 | 1/2008 | Nishigaki et al. | | |
| 2008/0032415 A1 | 2/2008 | Nishigaki et al. | | |
| 2008/0045736 A1* | 2/2008 | Ying et al. | .................... | 556/405 |

FOREIGN PATENT DOCUMENTS

| | | | |
|---|---|---|---|
| EP | 1790706 | A1 | 5/2007 |
| EP | 2093194 | A1 | 8/2009 |
| JP | 200328797 | A | 1/2003 |
| JP | 2003524147 | A | 8/2003 |
| JP | 200670250 | A | 3/2006 |
| WO | 0017642 | A2 | 3/2000 |
| WO | 2005123874 | A1 | 12/2005 |
| WO | 2007075495 | A2 | 7/2007 |
| WO | 2007078297 | A2 | 7/2007 |
| WO | 2008066138 | A1 | 6/2008 |

OTHER PUBLICATIONS

Grasset, F., et al., “Surface modification of zinc oxide nanoparticles by aminopropyltriethoxysilane”, 2003, J. Alloys and Compounds, pp. 298-311.*

Zhnag, Y., et al., “Protease-Modulated Cellular Uptake of Quantum Dots”, 2006, Nano Letters, pp. 1988-1992.*

International Search Report for PCT/JP2009/067643 mailed Nov. 17, 2009.

Written Opinion for PCT/JP2009/067643 mailed Nov. 17, 2009.

Moriyuki Sato et al, Preparation and properties of polymer/zinc oxide nanocomposites using functionalized zinc oxide quantum dots, European Polymer Journal, Sep. 18, 2008, vol. 44, Issue 11, pp. 3430-3438.

Jianwen Zhao et al., Fabrication of micropatterned ZnO/SiO2 core/shell nanorod arrays on a nanocrystalline diamond film and their application to DNA hybridization detection, J. Mater Chem., Mar. 31, 2008, vol. 18, pp. 2459-2465.

Extended European Search Report dated Jul. 12, 2012, corresponding to European patent application No. 09823469.3.

Office Action mailed Feb. 19, 2013, corresponding to Japanese patent application No. 2010-535747.

* cited by examiner

*Primary Examiner* — Michael G Hartley

*Assistant Examiner* — Lance Rider

(74) *Attorney, Agent, or Firm* — Lowe Hauptman & Ham, LLP

(57) ABSTRACT

Provided is a fluorescent labeling material, including zinc oxide nanoparticles each surface-modified with an organic compound having an amino group placed at an outer end thereof. Also provided is a fluorescent labeling agent to be used in vivo or in vitro, including the fluorescent labeling material, in which: EDC or the like is bound thereto through the amino group; and a substance capable of selectively binding to a target to be fluorescently labeled, such as an antibody, is linked thereto.

7 Claims, 19 Drawing Sheets
(3 of 19 Drawing Sheet(s) Filed in Color)

FT-IR spectrum of ZHP[40:1]

Powder XRD patterns

PL spectrum of ZHP[40:1] in methanol

Results of absorption and PL of ZHP[20:1-60:1] in methanol

| | Molar Ratio ZnO:HPA | Absorption[nm] | PL[nm] |
|---|---|---|---|
| | 20:1 | 314 | 506 |
| | 30:1 | 322 | 522 |
| ZHP | 40:1 | 335 | 522 |
| | 50:1 | 314 | 512 |
| | 60:1 | 317 | 513 |

FT-IR spectrum of ZHI[40:1]

PL spectrum of ZHI[40:1] in methanol

Powder XRD patterns

Results of absorption and PL of ZHI[20:1-60:1] in methanol

| | Molar Ratio ZnO:HPA | Absorption[nm] | PL[nm] |
|---|---|---|---|
| | 20:1 | 344 | 410,453,512 |
| | 30:1 | 292,354,409 | 363,418,446,519 |
| ZHI | 40:1 | 341 | 418,446,514 |
| | 50:1 | 341,386 | 517 |
| | 60:1 | 297,349 | 420,451,517 |

TG data of ZHI[20:1-60:1]

| | Molar Ratio ZnO:HPA | Final Reduction Ratio [%] |
|---|---|---|
| | 20:1 | 32.6 |
| | 30:1 | 33.9 |
| ZHI | 40:1 | 33.6 |
| | 50:1 | 28.3 |
| | 60:1 | 20.2 |

FT-IR spectrum of ZHIE40:1

Powder XRD patterns

PL spectrum of ZHIE[40:1] in methanol

UV-vis spectrum of ZHIE[40:1] in methanol

Results of absorption and PL at ZHIE[20:1-60:1] in methanol

| | Molar Ratio ZnO:HPA | Absorption[nm] | PL[nm] |
|---|---|---|---|
| ZHIE | 20:1 | 340,370 | 411,502 |
| | 30:1 | 303,356 | 429,524 |
| | 40:1 | 348 | 412,532 |
| | 50:1 | 345,370 | 525 |
| | 60:1 | 306,353 | 413,532 |

TEM image of ZHIE40:1

| BLUE COLOR | GREEN COLOR | RED COLOR |
|---|---|---|
| FLUORESCENCE WAVELENGTH λEM (435-485nm) | FLUORESCENCE WAVELENGTH λEM (510-560nm) | FLUORESCENCE WAVELENGTH λEM (600-620nm) |
| EXCITATION WAVELENGTH λEX (340-380nm) | EXCITATION WAVELENGTH λEX (460-500nm) | EXCITATION WAVELENGTH λEX (570-590nm) |
| DICHROIC MIRROR λDIC (400nm) | DICHROIC MIRROR λDIC (505nm) | DICHROIC MIRROR λDIC (600nm) |

FLUORESCENCE OBSERVATION OF MEMBRANE SURFACE ANTIGEN (Mac-1) OF MOUSE MACROPHAGE (Raw264.7)

UV-vis spectra of ZGAIE[40:1] in methanol

PL spectra of ZGAIE[40:1] in methanol

FT-IR-spectra of ZGAIE [40:1]

FLUORESCENT LABELING MATERIAL AND FLUORESCENT LABELING AGENT

CROSS-REFERENCE TO RELATED APPLICATION

This application is a continuation of International Application No. PCT/JP2009/067643, filed on Oct. 9, 2009.

TECHNICAL FIELD

The present invention relates to a fluorescent labeling material and a fluorescent labeling agent, in particular, a fluorescent labeling material using a material free of toxicity on living organisms and a fluorescent labeling agent using the fluorescent labeling material.

BACKGROUND ART

In recent years, technologies for fluorescently labeling biological cells and the like have been attracting attention, and technologies involving the use of the nanoparticles of cadmium selenide (CdSe) and zinc oxide (ZnO) as light emission sources have started to be developed. Both of CdSe and zinc oxide are suitable as light emission sources because: CdSe can serve as a quantum dot to develop a desired color and has a sharp spectrum; and zinc oxide is a material free of toxicity on living organisms.

CITATION LIST

Patent Literature

[PTL 1] JP 2003-28797 A
[PTL 2] JP 2003-524147 A
[PTL 3] JP 2006-70250 A
[PTL 4] WO 2005/123874 A1
[PTL 5] WO 2008/066138 A1

SUMMARY OF INVENTION

Technical Problem

CdSe is an excellent light emission source indeed, but involves the following problem owing to its toxicity on living organisms. Conditions under which CdSe is used and objects of labeling are limited.

Upon labeling of a living organism, a light emission source must be caused to selectively adhere to the target. In this case, there arises a need for modifying a nanoparticle serving as the light emission source with an antibody or the like through a proper binder.

The binder as a modifying material is preferably organic matter from the viewpoint of a binding reaction because the kinds of targets, and by extension, the kinds of antibodies and the like are various. Meanwhile, good crystallinity is needed when zinc oxide is considered to be a fluorescent light-emitting material.

However, inorganic crystals including, but not limited to, zinc oxide each involve the following problem. The more regular the crystal structure of any such inorganic crystal, the higher the difficulty with which the surface of the crystal is modified or bound with organic matter. In other words, there has arisen such a problem that surface-modified inorganic matter is so instable that it is difficult to develop a fluorescent labeling agent which brings together stability and light-emitting property.

The present invention has been made in view of the foregoing, and an object of the present invention is to provide a fluorescent labeling material and a fluorescent labeling agent each of which realizes stable fluorescent labeling of a living organism while using an inorganic crystal free of toxicity on living organisms as a light emission source.

Solution to Problem

In order to achieve the above-mentioned object, a fluorescent labeling material according to at least one embodiment includes zinc oxide nanoparticles each surface-modified with an organic compound having an amino group placed at an outer end thereof.

That is, in the invention according to at least one embodiment, various substances such as an antibody capable of selectively binding to a target to be fluorescently labeled can each be easily bound to a particle side through an amino group while a light emission source free of toxicity on living organisms is used. As a result, the number of objects to be fluorescently labeled can be increased.

It should be noted that the term “outer end” refers to a side opposite to the side on which the substance is bound to the particle, i.e., the outside when viewed from the particle. In addition, the term “zinc oxide nanoparticle” as used herein can be interpreted as a zinc oxide nanocrystal in a sense that the nanoparticle must have crystallinity to such an extent as to emit fluorescence. In addition, each molecule of the organic compound and each of the zinc oxide nanoparticles are not bound to each other at a ratio of 1:1, but instead a plurality of molecules of the organic compound are bound so as to cover the surface of each of the zinc oxide nanoparticles.

Further, a fluorescent labeling material according to at least one embodiment is a fluorescent labeling, in which the organic compound has an amide group and a urethane group.

That is, an improvement in color development efficiency or luminous efficiency can be expected from at least one embodiment of the present disclosure because of the presence of the amide group and urethane group each serving as an auxochrome. It should be noted that both the groups preferably exist so as to be adjacent to each other from the viewpoint of a band gap.

Further, a fluorescent labeling material according to at least one embodiment is a fluorescent labeling, in which the organic compound and each of the zinc oxide nanoparticles are bound to each other through an ester bond.

That is, according to at least one embodiment, a stable light emission source having a strong bond can be obtained by simultaneously performing the formation of nanoparticles and surface modification by a wet method involving the use of, for example, zinc acetate as a starting material. In other words, a light emission source whose surface is modified with an ester bond can be easily obtained. Particle diameters can be adjusted by controlling, for example, a concentration, a reaction time, and a reaction temperature. In addition, when the wet method is adopted, variations in the particle diameters are suppressed, and hence good monodisperse particles having a narrow particle size distribution can also be obtained.

Further, a fluorescent labeling material according to at least one embodiment is a fluorescent labeling material in which the organic compound includes a binding chain represented by the following formula.

(1)

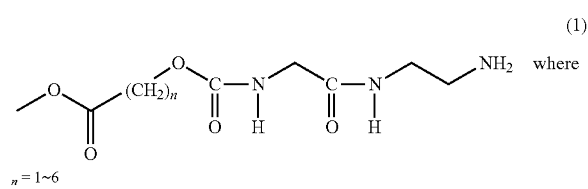

That is, according to at least one embodiment, various substances such as an antibody capable of selectively binding to a target to be fluorescently labeled can each be easily bound to a particle side through an amino group by using a fluorescent labeling material free of toxicity on living organisms. In addition, an improvement in color development efficiency or luminous efficiency can be expected because an amide group and a urethane group each serving as an auxochrome exist so as to be adjacent to each other. In addition, a stable light emission source having a strong bond can be obtained by simultaneously performing the formation of nanoparticles and surface modification by means of zinc acetate as a starting material.

The reason why n is set equal to 1 to 6 here is as described below. When n is small, the compound has so good solubility in water as to be suitable for biological labeling. When n exceeds 6, the handleability of the compound deteriorates. In addition, electrons are each requested to transfer by up to about 50 nm from the viewpoint of light-emitting property. In consideration of the request as well, an upper limit for n is 6. It should be noted that n more preferably equals 1 to 4.

Further, a fluorescent labeling material according to at least one embodiment is a fluorescent labeling material in which the fluorescent labeling material has a particle diameter of 15 nm or less.

That is, according to at least one embodiment the fluorescent labeling of minute biological tissues or biological substances including targets in capillaries is enabled. It should be noted that zinc oxide crystal particles each having a particle diameter of the order of single nanometers to about ten or so nanometers can be obtained by a sol-gel method or the like.

Further, a fluorescent labeling material according to at least one embodiment is a fluorescent labeling material in which the zinc oxide nanoparticles each have crystallinity with which the nanoparticle emits fluorescence.

That is, according to at least one embodiment, labeling by utilizing a light-emitting characteristic originating from the so-called crystallinity is enabled. Light having any wavelength may be used as excitation light as long as the wavelength falls within such a region as to be free of any particular influence on biological labeling. Excitation may be performed with ultraviolet light, and visible light is also permitted in some cases. A light source is, for example, a pulse laser such as helium-cadmium laser (325 nm) capable of continuous oscillation or nitrogen laser (having a wavelength of 337 nm), or an ultraviolet lamp such as a mercury lamp. It should be noted that upon observation, the fluorescence can be observed as light emission having a predetermined color such as a blue, green, orange, or red color through a filter as appropriate.

Further, a fluorescent labeling agent according to at least one embodiment is a fluorescent labeling agent to be used in vivo or in vitro, including the fluorescent labeling material in which: 3-[(2-aminoethyl)dithio]propionic acid (AEDP), 4-(p-azidosalicylamido)butylamine (ASBA), 1-ethyl-3-[3-dimethylaminopropyl]carbodiimide hydrochloride (EDC), or EDC to which N-hydroxysulfosuccinimide (Sulfo-NHS) is added is bound thereto through the amino group; and a substance capable of selectively binding to a target to be fluorescently labeled is linked thereto.

That is, according to at least one embodiment, a fluorescent labeling agent can be provided which: can easily bind to a particle side; and suitably binds not only to a substance capable of selectively binding to a target but also to a substance that can be phagocytosed by, for example, a macrophage to realize easy labeling. Sulfo-NHS is added as a stabilizer. It should be noted that the procedure for binding is not particularly limited. That is, the fluorescent labeling material and EDC or the like may be bound to each other first before the substance capable of selectively binding to the target is linked. Alternatively, EDC or the like and the substance capable of selectively binding to the target may be linked to each other first before the fluorescent labeling material is bound.

Further, a fluorescent labeling agent according to at least one embodiment is a fluorescent labeling agent in which the substance capable of selectively binding to a target is an antibody, an enzyme, a lectin, or a nucleic acid.

That is, according to at least one embodiment, easy recognition of a target disease or the like in a biopsy or the like is enabled. The term "nucleic acid" naturally comprehends DNA and RNA. Other examples of the substance capable of selectively binding to the target include physiologically active substances (such as a hormone, a cytokine, and a growth factor), receptors, glucides (carbohydrates), and lipids.

Further, at least one embodiment of the present disclosure is a use of the fluorescent labeling, including using as a target a tumor cell, a leukemia cell, a virus-infected cell, or a normal cell, a protein, an enzyme, or a nucleic acid.

That is, according to at least one embodiment easy recognition of a tumor or the like is enabled. The term "tumor cell" comprehends both benign and malignant cells. In addition, according to at least one embodiment easy recognition of various biological substances not only on a cell surface but also in a cell cytoplasm is enabled.

Advantageous Effects of Invention

According to the present invention, there can be provided a fluorescent labeling material capable of easily binding each of various substances such as an antibody capable of selectively binding to a target to be fluorescently labeled to a particle side through an amino group while using zinc oxide free of toxicity on living organisms. In addition, a stable fluorescent labeling agent based on the material can be prepared.

In particular, the present invention has the following advantages as well. The present invention can be prepared with a commercially available reagent, and is excellent in industrial mass productivity (can be produced at a low cost).

BRIEF DESCRIPTION OF DRAWINGS

The patent or application file contains at least one drawing executed in color. Copies of this patent or patent application publication with color drawing(s) will be provided by the Office upon request and payment of the necessary fee.

FIGS. 18-2, 18-4, 19-2, 20-2, 21-2, 22-2, and 23-2 are views drawn on the basis of the above-mentioned respective views. It should be noted that in each of the views illustrated in gray scales, a contrast and brightness are adjusted as appropriate in order that clear display may be achieved. Views or photographs illustrated in gray scales are submitted in designated states as required.

FIG. 1 is a view illustrating a scheme for preparing ZHP with zinc acetate and hydroxypropionic acid.

FIG. 2 is a view illustrating a scheme for preparing ZHI from ZHP.

FIG. 3 is a view illustrating a scheme for preparing ZHIE from ZHI.

FIG. 4 is a view illustrating the result of the measurement of the FT-IR spectrum of ZHP.

FIG. 18-1 is a TEM photograph of ZHIE.

FIG. 18-2 is a view illustrating the way FIG. 18-1 is seen.

FIG. 18-3 is a TEM photograph of ZHIE.

FIG. 18-4 is a view illustrating the way FIG. 18-3 is seen.

FIG. 19-1 is a photograph showing the manner in which a solution of ZHIE in water emits light when irradiated with ultraviolet light.

FIG. 19-2 is a view illustrating the way FIG. 19-1 is seen.

FIG. 20-1 are photographs each obtained by observing fluorescence from a fluorescent labeling agent (zymosan to which zinc oxide nanoparticles are bound), the fluorescence being achieved by the application of excitation light changed from ultraviolet light to visible light, as blue light emission, green light emission, or red light emission through a filter.

FIG. 20-2 are views illustrating the way FIGS. 20-1 are seen.

FIG. 21-1 are photographs each obtained by observing the phagocytic action of a cell through fluorescent labeling. The left photograph shows the result of fluorescence observation with a confocal laser scanning microscope. The right photograph is obtained by superimposing the results of optical observation in a bright field and the fluorescence observation.

FIG. 21-2 are views illustrating the way FIGS. 21-1 are seen.

FIG. 22-1 is a photograph confirming by a phagocytic action that a fluorescent labeling agent does not lose its fluorescent characteristic even when the agent flows in the blood in a living organism.

FIG. 22-2 is a view illustrating the way FIG. 22-1 is seen.

FIG. 23-1 are photographs each obtained by observing an Raw264.7 cell membrane antigen through fluorescent labeling. The left photograph shows the result of optical observation in a bright field. The central photograph shows the result of a control experiment with an unlabeled anti-Mac-1 antibody. The right photograph shows the result of fluorescence observation with a fluorescent labeling agent of the present invention (anti-Mac-1 antibody to which zinc oxide nanoparticles are bound).

FIG. 23-2 are views illustrating the way FIGS. 23-1 are seen.

DESCRIPTION OF EMBODIMENTS

Embodiment 1

Hereinafter, the embodiments of the present invention are described in detail with reference to drawings. In Embodiment 1, the case where n in the chemical formula (1) equals 2 is described. Specifically, an example in which a fluorescent labeling material named ZHIE by the inventors of the present invention was prepared with a commercially available reagent at a low cost with facility is described. Next, an example in which the phagocytic action or the like of a mouse macrophage on zymosan is actually observed by preparing a fluorescent labeling agent with the fluorescent labeling material is described. Finally, the fact that ZHIE is a fluorescent labeling material with extremely high general-purpose property is described by proving ZHIE free of toxicity.

A fluorescent labeling material of Embodiment 1 can be produced by the following method.

Figure 1:
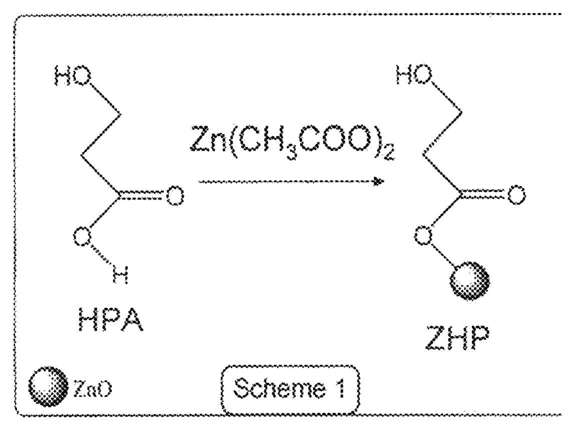
FIGS. 18-1, 18-3, 19-1, 20-1, 21-1, 22-1, and 23-1 illustrate photographs in gray scale.

(1) Organic matter whose terminals are OH groups is introduced onto the surface of a zinc oxide crystal of several nanometers in size by using a zinc compound having a high solubility as a starting material (FIG. 1). In this case, the formation of crystal particles and surface modification are simultaneously performed by a wet method so that a composite having a strong bond may be prepared. In other words, a zinc oxide nanocrystal is not additionally modified with the organic matter later, but instead a novel zinc oxide nanocrystal having a functional group from the beginning is synthesized.

Figure 2:
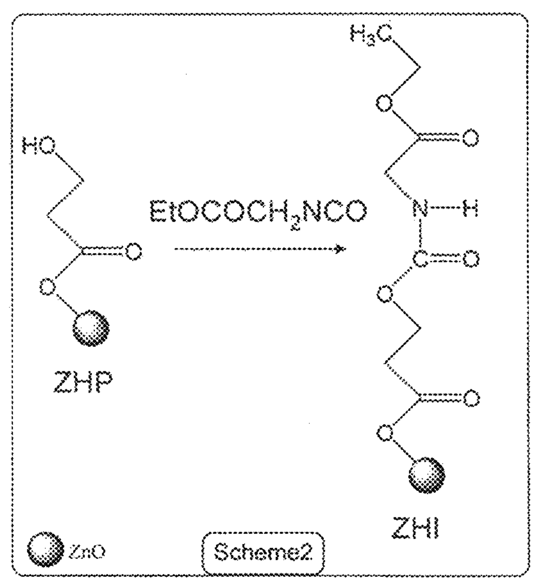

(2) Next, organic matter having an isocyanate group and an ester group is used so that the OH group at the terminal and the isocyanate group may be caused to react with each other (FIG. 2). As a result, a urethane group as a first auxochrome is introduced.

Figure 3:
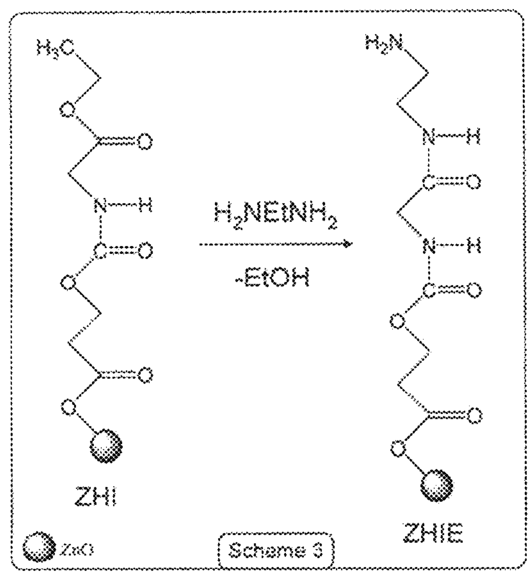

(3) Next, an amidation reaction is performed with a hydrocarbon compound having amino groups at both terminals so that an amide group as a second auxochrome may be introduced. Thus, zinc oxide nanoparticles having amino groups at their outer ends are prepared (FIG. 3).

<Preparation of Fluorescent Labeling Material ZHIE: Preparation of ZHP>

First, 5.488 g (0.025 mol) of zinc acetate dihydrate (manufactured by Wako Pure Chemical Industries, Ltd.) were added to and dissolved in 250 ml of absolute ethanol (manufactured by Wako Pure Chemical Industries, Ltd.), and then the solution was distilled at 80° C. over 3 hours. The operation was terminated when the volume of a residual liquid in a flask became 100 ml (the volume of a distillate became 150 ml).

Moisture was removed from 0.1126 g (0.00125 mol) of 3-hydroxypropionic acid (HPA) (manufactured by TOKYO CHEMICAL INDUSTRY CO., LTD.) with an evaporator. The remainder was added to the above-mentioned residual liquid (condensate), and then the mixture was refluxed at 80° C. for 1 hour. The resultant is defined as a solution 1.

Next, a product prepared in advance by adding 1.486 g (0.035 mol) of lithium hydroxide monohydrate (manufactured by Wako Pure Chemical Industries, Ltd.) to 150 ml of absolute ethanol, stirring the mixture for 4 hours to 5 hours, and cooling the mixture to 0° C. was added to the solution 1, and then the resultant mixture was subjected to an ultrasonic treatment for 15 minutes.

Figure 4:
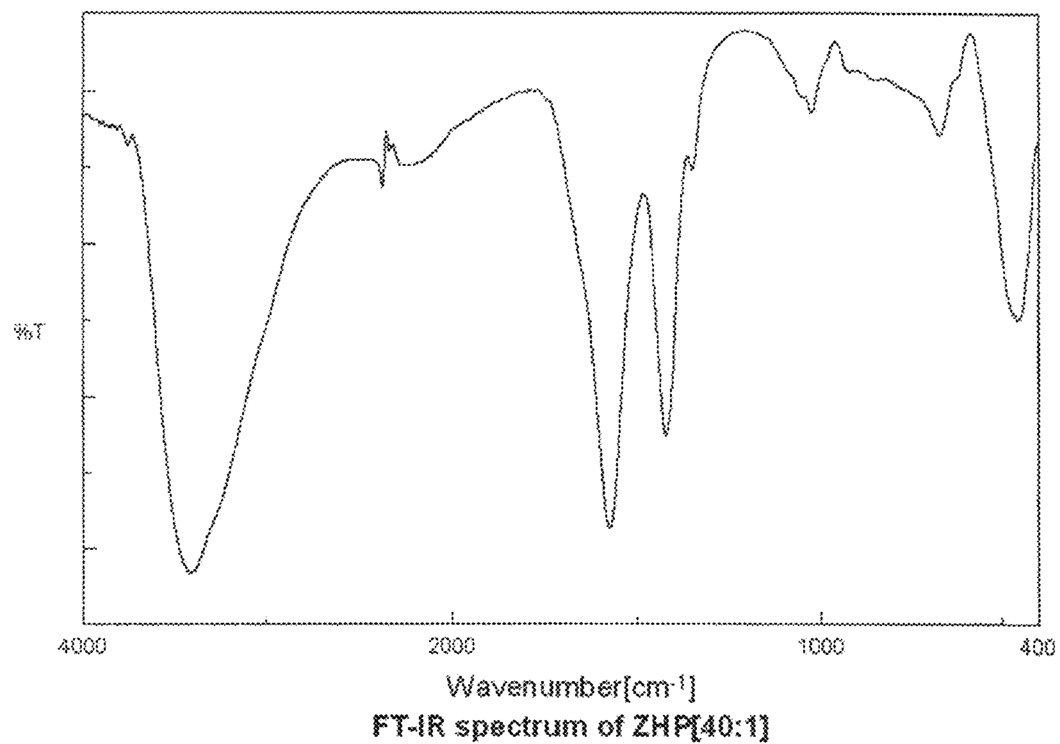
Figure 5:
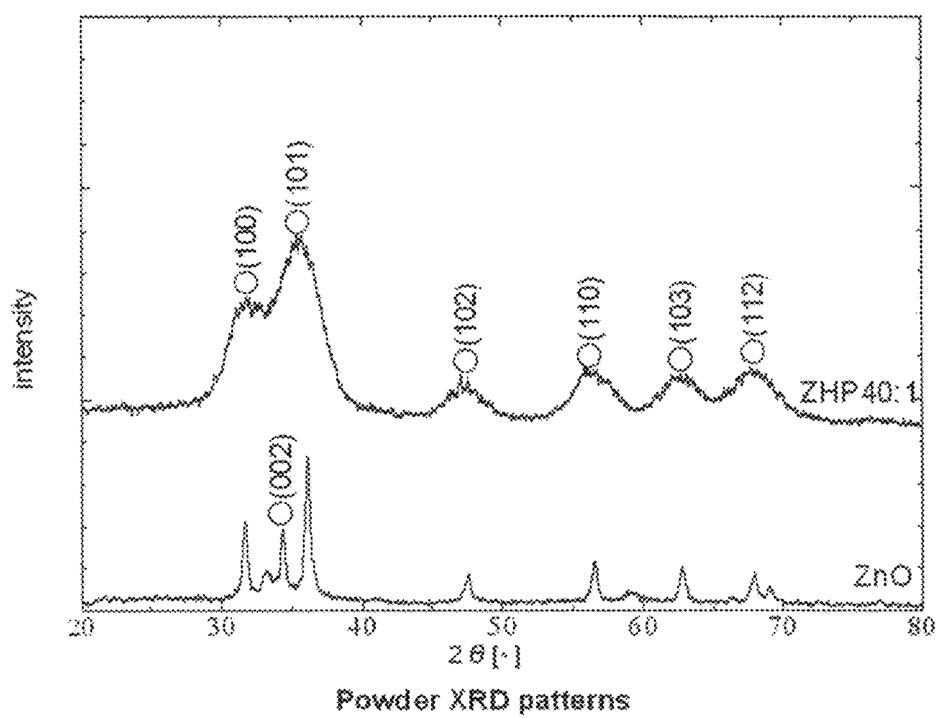
FIG. 5 is a view illustrating the XRD pattern of ZHP.

Acetone was added to the treated liquid to produce a precipitate, and then centrifugal separation was performed. After that, the resultant was dried under reduced pressure at 40° C. Thus, a white powder was obtained. The powder was considered to be a zinc oxide nanocrystal modified with 3-hydroxypropionic acid illustrated on the right side of FIG. 1. The measurements of the FT-IR spectrum (FIG. 4) and XRD pattern (FIG. 5) of the powder confirmed that the zinc oxide nanocrystal modified with 3-hydroxypropionic acid was prepared indeed.

Although FIG. 1 illustrates the substance in such a manner that the surface of the zinc oxide nanocrystal is modified with one molecule of 3-hydroxypropionic acid, a large number of molecules of 3-hydroxypropionic acid are actually bound to the surface so as to form a coating. Hereinafter, the substance is represented as ZHP as appropriate. Although the foregoing result was obtained by preparation with such amounts of ZnO and HPA that a molar ratio "ZnO:HPA" was 40:1, it was confirmed that the preparation was similarly attained even by setting the ratio to 20:1, 30:1, 50:1, or 60:1.

Figure 6:
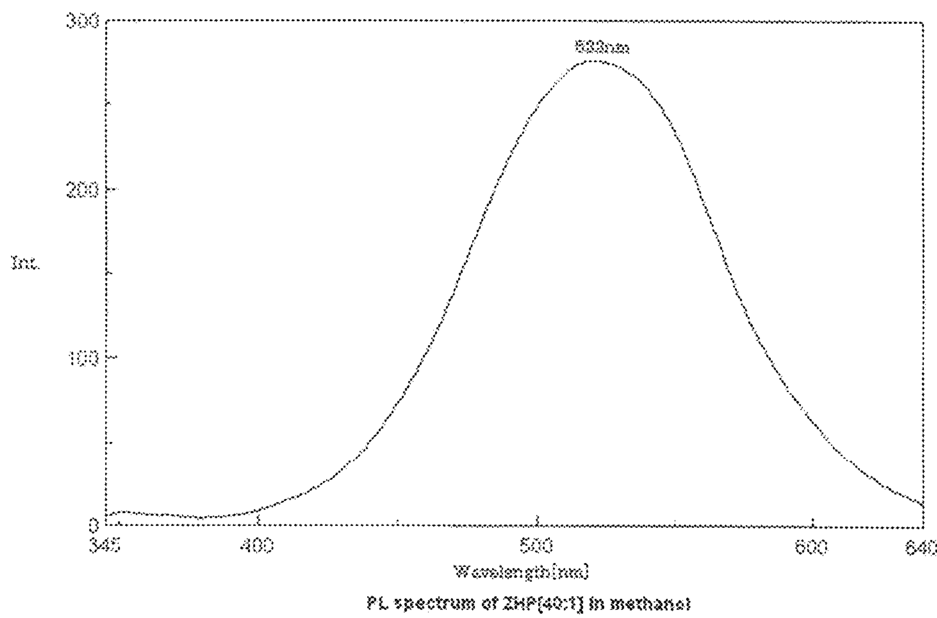
FIG. 6 is a view illustrating the result of the measurement of the fluorescent spectrum of ZHP in methanol.
Figures 7, 8:
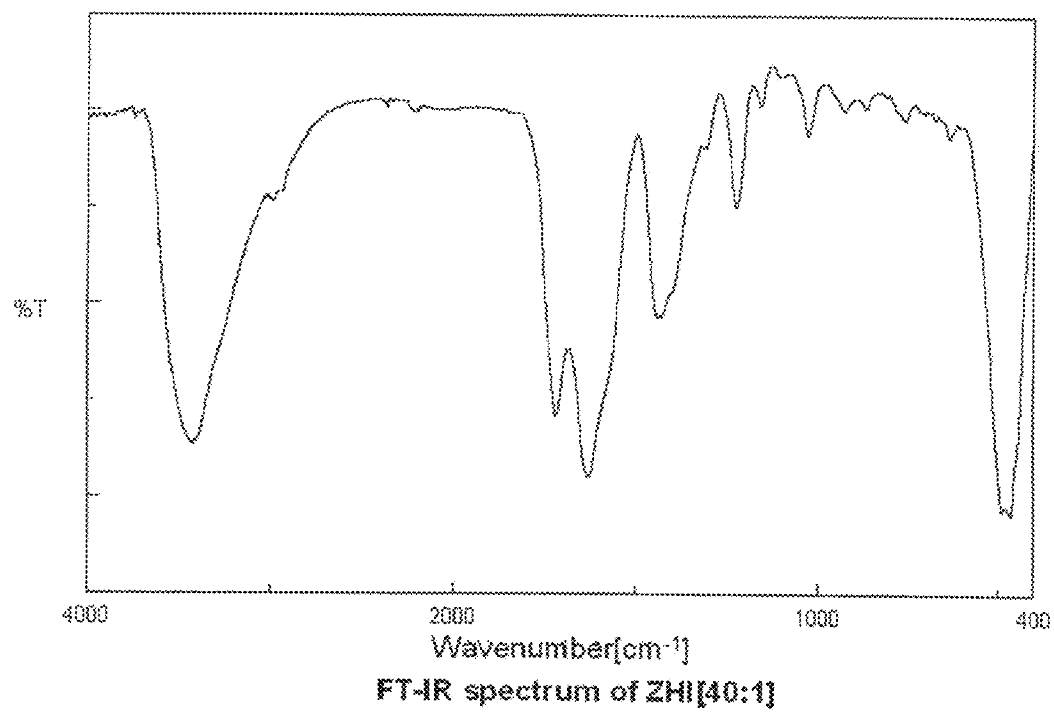
FIG. 7 is a table showing the peak wavelength and absorption wavelength of the fluorescent spectrum of ZHP depending on a difference in synthesis ratio.
FIG. 8 is a view illustrating the result of the measurement of the FT-IR spectrum of ZHI.

Next, the fluorescent spectrum of ZHP in methanol was measured. As illustrated in FIG. 6, ZHP was confirmed to emit green light. As a result, it was able to be confirmed that the zinc oxide nanoparticles in ZHP each had crystallinity with which the nanoparticle emitted fluorescence. It should be noted that FIG. 7 shows the peak wavelength of a fluorescent spectrum obtained by using ZHP prepared by altering the molar ratio. It should be noted that the figure shows a local maximum absorption wavelength at the same time.

<Preparation of Fluorescent Labeling Material ZHIE: Preparation of ZHI>

ZHP has an OH group at an outer end thereof. Next, ZHI is prepared from ZHP by utilizing the OH group (FIG. 2). 0.5 Gram of ZHP (prepared at a ratio "ZnO:HPA" of 40:1) was added to 5 ml of N,N-dimethylacetamide (manufactured by Wako Pure Chemical Industries, Ltd.), and then the mixture was subjected to an ultrasonic treatment so that ZHP might be dispersed well. After that, a ten-fold molar amount of ethyl acetate isocyanate ester (manufactured by Tokyo Kagaku Kougyou Co., Ltd.) with respect to HPA was added dropwise while the dispersed solution was stirred. Five drops of triethylamine (manufactured by Wako Pure Chemical Industries, Ltd.) were added as a catalyst to the dispersed solution, and then the dispersed solution was stirred at normal temperature for 2 hours. After that, the dispersed solution was refluxed at 100° C. for 20 hours. Particles in the dispersed solution were washed under stirring with methanol twice, followed by centrifugal separation. Thus, a white powder was obtained.

The powder was considered to be a zinc oxide nanocrystal whose surface was modified with a binding chain represented by the following formula (see FIG. 2).

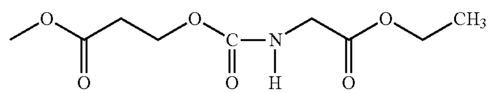 [SMILES: CCOC(=O)CNC(=O)OCCC(=O)OC]

Figure 9:
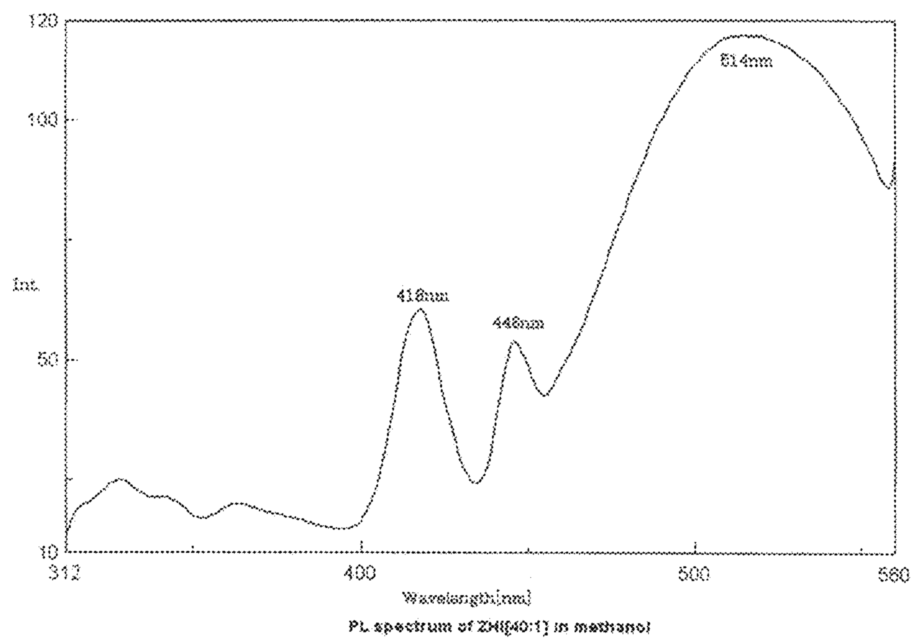
FIG. 9 is a view illustrating the XRD pattern of ZHI.

The measurements of the FT-IR spectrum (FIG. 8) and XRD pattern (FIG. 9) of the powder confirmed that the zinc oxide nanocrystal whose surface was modified with the above-mentioned binding chain was prepared indeed.

Although FIG. 2 illustrates the substance in such a manner that the surface of the zinc oxide nanocrystal is modified with one molecule of the above-mentioned organic matter, a large number of molecules of the organic matter are actually bound to the surface so as to form a coating. Hereinafter, the substance is represented as ZHI as appropriate. Although the foregoing result was obtained by preparation with such amounts of ZnO and HPA that a molar ratio "ZnO: HPA" was 40:1 in terms of HPA, it was confirmed that the preparation of ZHI was similarly attained even by setting the ratio to 20:1, 30:1, 50:1, or 60:1.

Figure 10:
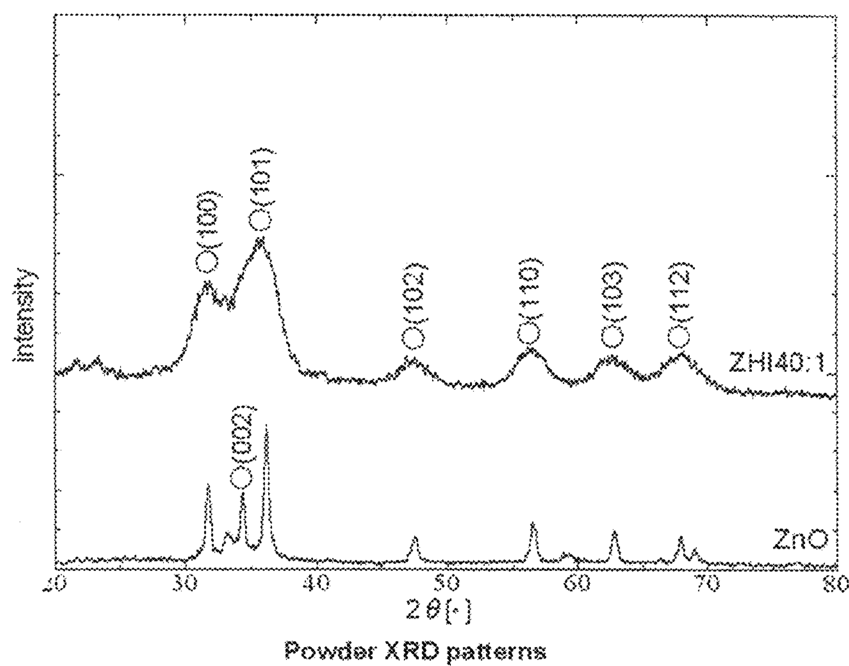
FIG. 10 is a view illustrating the result of the measurement of the fluorescent spectrum of ZHI in methanol.
Figures 11, 12, 13:
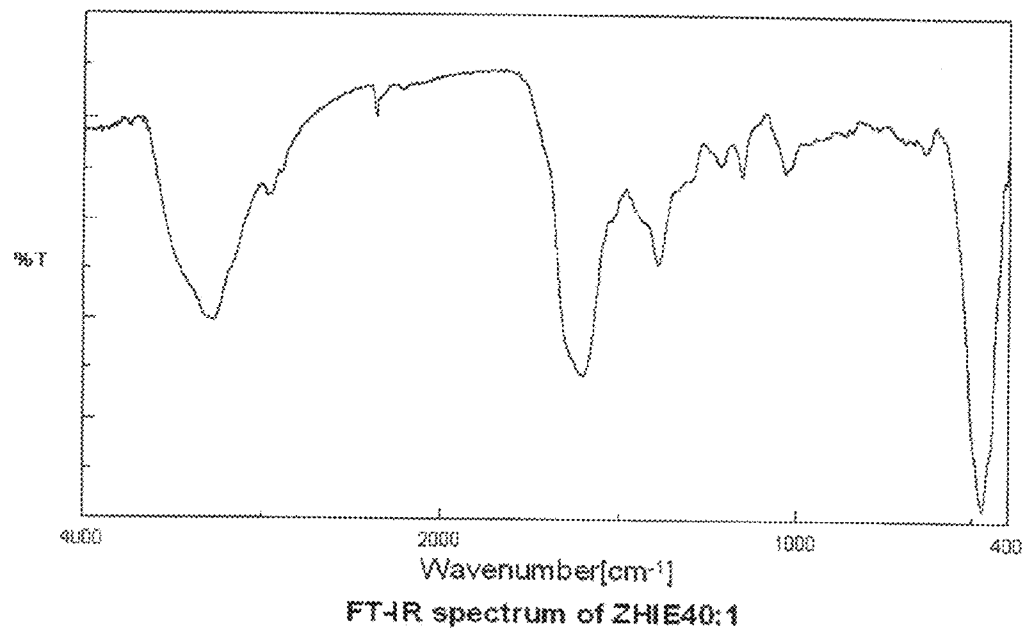
FIG. 11 is a table showing the peak wavelength and absorption wavelength of the fluorescent spectrum of ZHI depending on a difference in synthesis ratio.
FIG. 12 is a table showing the results of the measurement of the minimum reduction ratio of ZHI in a TD/DTA measurement depending on a difference in synthesis ratio.
FIG. 13 is a view illustrating the result of the measurement of the FT-IR spectrum of ZHIE.

Next, the fluorescent spectrum of ZHI in methanol was measured. As illustrated in FIG. 10, ZHI was able to be confirmed to emit substantially green light. As a result, it was able to be confirmed that the zinc oxide nanoparticles in ZHI each still had crystallinity with which the nanoparticle emitted fluorescence. It should be noted that FIG. 11 shows the peak wavelength of the fluorescent spectrum of ZHI prepared by altering the molar ratio. It should be noted that the figure shows a local maximum absorption wavelength at the same time.

It should be noted that FIG. 12 shows the results of the measurement of the minimum reduction ratio of ZHI prepared from different molar ratios in a TD/DTA measurement. As is apparent from the figure, the final reduction ratio reduces as the amount of the organic matter increases from 60:1 to 40:1, but the final reduction ratio remains nearly unchanged from 40:1 to 20:1. As a result, it was able to be confirmed that a limit for the amount of the organic matter capable of binding to the surface of ZnO fell within the molar ratio range of about 1/40 to 1/50 with respect to ZnO.

<Preparation of Fluorescent Labeling Material ZHIE: Preparation of ZHIE>

Since ZHI had an ester group in the vicinity of its outside, the group was subjected to an amidation reaction so that an amide group might be introduced. In addition, an amino group was introduced into an outer end in order that binding property with an antibody or the like might be improved. That is, ZHIE was prepared from ZHI (FIG. 3).

0.2 Gram of ZHI (prepared at a ratio "ZnO:HPA" of 40:1) was added to 5 ml of dimethylsulfoximide (manufactured by TOKYO CHEMICAL INDUSTRY CO., LTD.), and then the mixture was subjected to an ultrasonic treatment so that ZHI might be dispersed well. After that, a ten-fold molar amount of ethylenediamine (manufactured by Kanto Chemical Co., Inc.) with respect to HPA was added dropwise while the dispersed solution was stirred. The resultant was refluxed at 100° C. for 2 hours. After that, the resultant was cooled to 0° C., and then a pressure was reduced for 10 minutes so that ethanol as a by-product might be removed. The foregoing operation was repeated every one hour a total of six times. Particles in the dispersed solution were washed under stirring with acetone twice, followed by centrifugal separation. Thus, a white powder was obtained.

The powder was considered to be a zinc oxide nanocrystal whose surface was modified with a binding chain represented by the following formula (see FIG. 3).

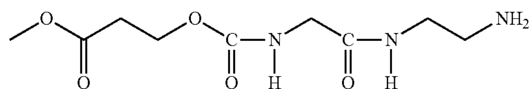 [SMILES: COC(=O)CCOC(=O)NCC(=O)NCCN]

Figure 14:
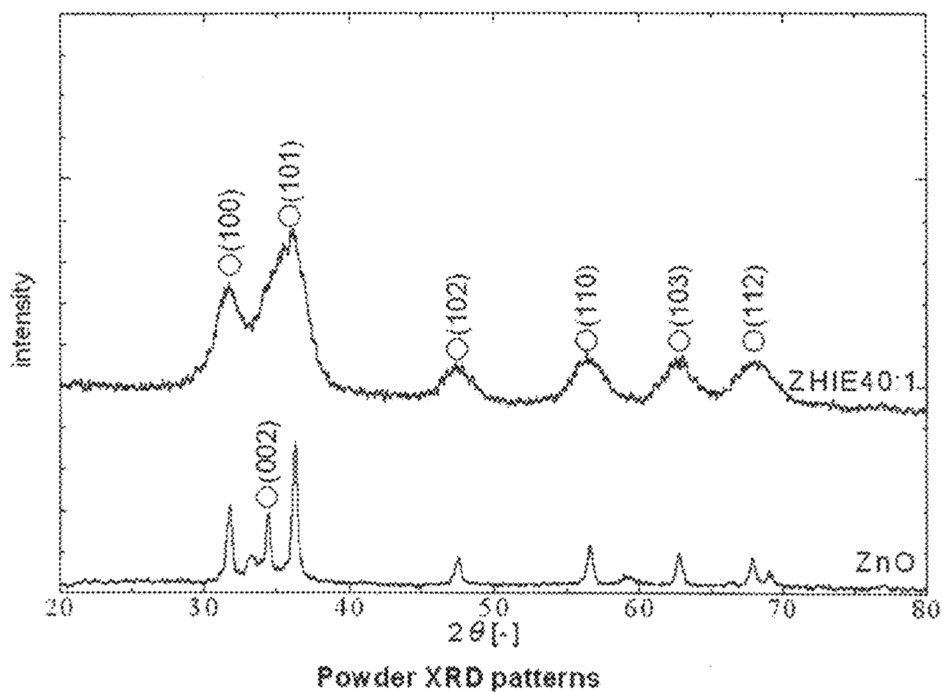
FIG. 14 is a view illustrating the XRD pattern of ZHIE.

The measurements of the FT-IR spectrum (FIG. 13) and XRD pattern (FIG. 14) of the powder confirmed that the zinc oxide nanocrystal whose surface was modified with the above-mentioned binding chain was prepared indeed. This is the binding chain in the case where n in the chemical formula (1) equals 2.

Although FIG. 3 illustrates the substance in such a manner that the surface of the zinc oxide nanocrystal is modified with one molecule of the above-mentioned organic matter having amino groups at the terminals, a large number of molecules of the organic matter are actually bound to the surface so as to form a coating. Hereinafter, the substance is represented as ZHIE as appropriate. Although the foregoing result was obtained by preparation with such amounts of ZnO and HPA that a molar ratio "ZnO:HPA" was 40:1 in terms of HPA, it was confirmed that the preparation of ZHIE was similarly attained even by setting the ratio to 20:1, 30:1, 50:1, or 60:1.

Figure 15:
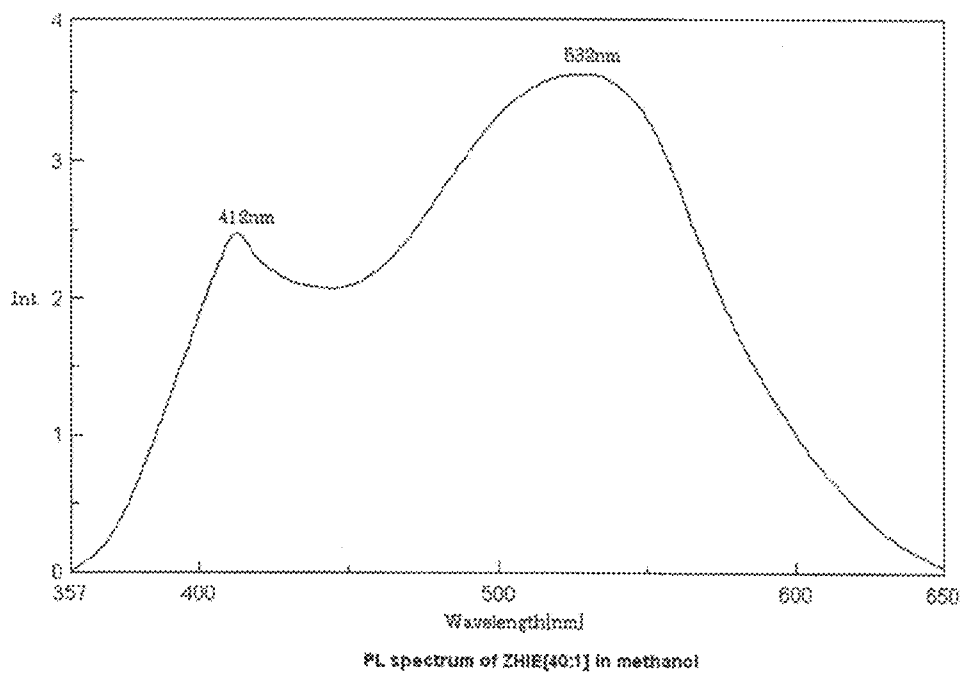
FIG. 15 is a view illustrating the result of the measurement of the fluorescent spectrum of ZHIE in methanol.
Figures 16, 17:
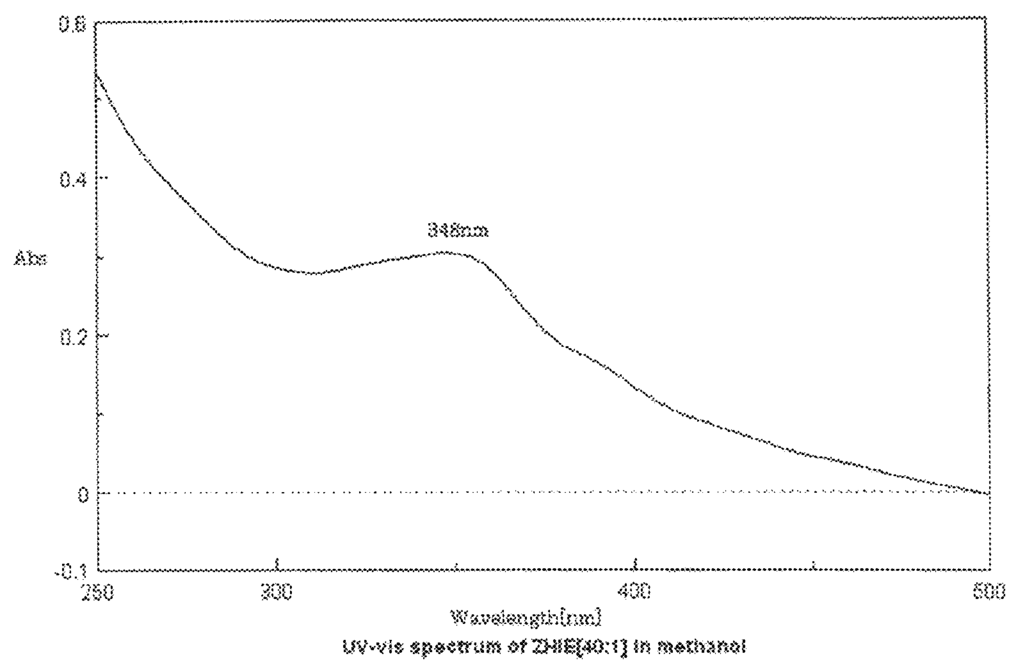
FIG. 16 is a view illustrating the result of the measurement of the absorption spectrum of ZHIE.
FIG. 17 is a table showing the peak wavelength and absorption wavelength of the fluorescent spectrum of ZHIE depending on a difference in synthesis ratio.

Next, the fluorescent spectrum of ZHIE in methanol was measured. As illustrated in FIG. 15, ZHIE was able to be confirmed to emit substantially green light. As a result, it was able to be confirmed that the zinc oxide nanoparticles in ZHIE each still had crystallinity with which the nanoparticle emitted fluorescence. Peaks are present at 412 nm and 532 nm, and are considered to be light emission based on an exciton and light emission based on a crystal defect, respectively. FIG. 16 illustrates the result of the measurement of an absorption spectrum. A peak is observed at 348 nm, and is considered to be based on exciton absorption.

It should be noted that FIG. 17 shows the peak wavelength of the fluorescent spectrum of ZHIE prepared by altering the molar ratio. It should be noted that the figure shows a local maximum absorption wavelength at the same time.

Figures 1, 3, 18:
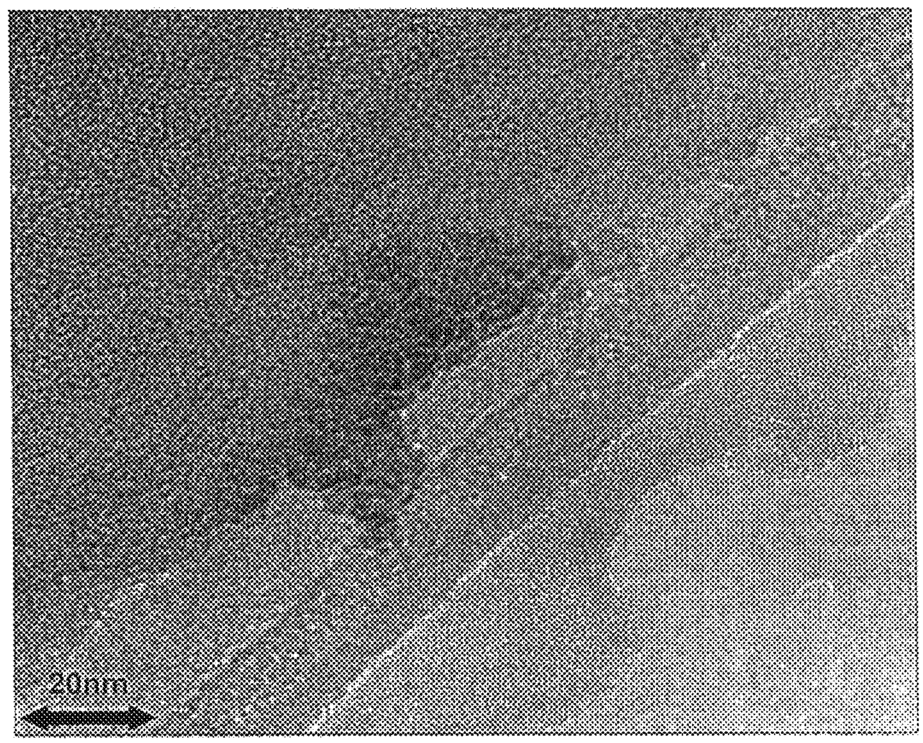
Figures 2, 18:
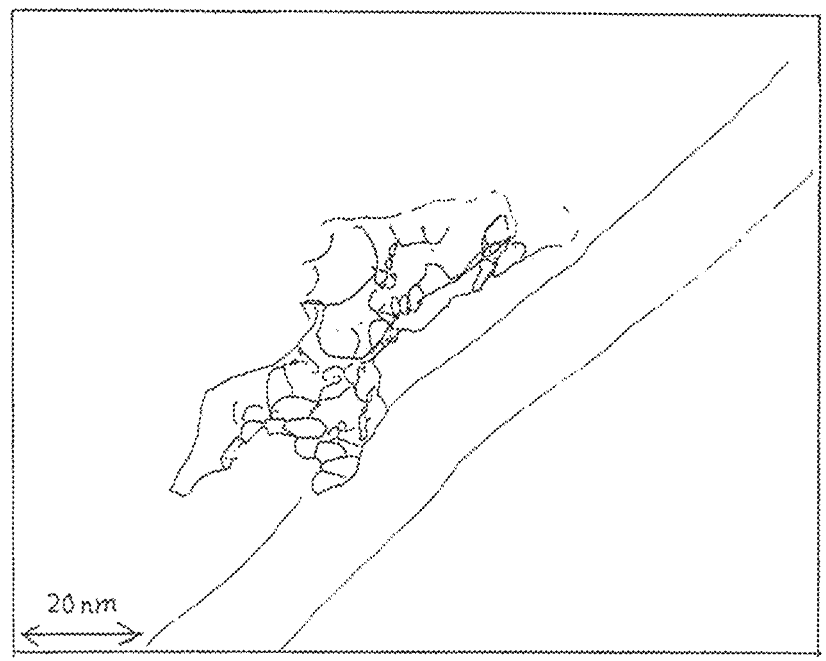
Figures 4, 18:
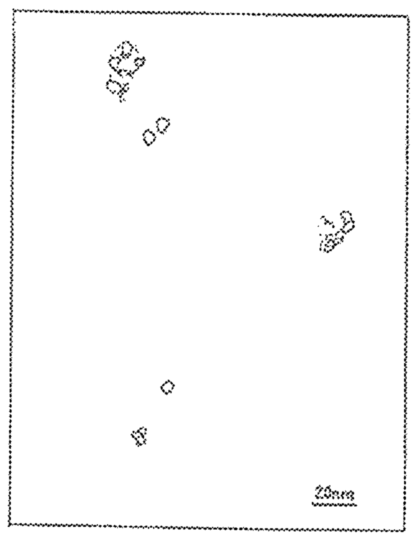

In addition, FIG. 18 show TEM photographs of ZHIE. FIG. 18-1 is a photograph obtained by photographing a mass portion. FIG. 18-3 is a photograph obtained by photographing dispersed small masses (part of which aggregate). However, it can be found that the small masses of ZHIE each have a size of the order of generally single nanometers, or specifically 5 nm to 6 nm. It should be noted that particle diameters measured by dispersing ZHIE in methanol were each about several nanometers to fifteen nanometers in size, and had an average particle diameter of 11.7 nm. Accordingly, it was able to be confirmed that the nanoparticles were dispersed in the liquid alone or in a state of being an aggregate of several nanoparticles.

Figures 1, 19:
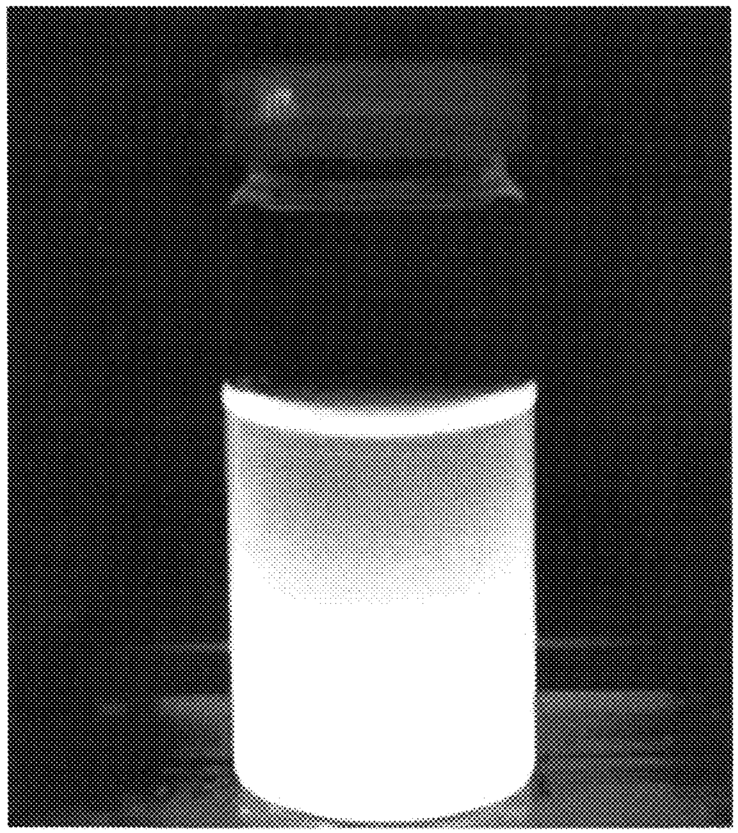

In addition, 5 mg of ZHIE were weighed, loaded into 20 ml of pure water, and dispersed by an ultrasonic treatment for 5 minutes. FIG. 19 show the manner in which the dispersed solution emits light upon application of UV light from below the solution.

The foregoing preparation approach was able to provide a fluorescent labeling material of about ten or so nanometers or less in size, the fluorescent labeling material emitting fluorescence in a visible light region and having a surface modified with an organic substance having an amino group placed at an outer end thereof. In particular, the material is excellent in mass productivity because the material can be prepared with a commercially available raw material. Although a preparation approach involving separately modifying each of the zinc oxide nanoparticles with the organic matter by means of a silane coupling agent is also possible, ZHIE obtained by the former approach is more stable because a binding force between the organic matter and each of the zinc oxide nanoparticles is larger. In addition, ZHIE described above is expected to have high luminous efficiency as well because an amide group and a urethane group each serving as an auxochrome exist and are adjacent to each other.

<Preparation Example 1 of Fluorescent Labeling Agent with ZHIE>

Next, a fluorescent labeling agent to be used in vivo or in vitro was prepared with ZHIE. Described here is a method of preparing such a fluorescent labeling agent that zymosan is used as a substance capable of selectively binding to a target and the substance is bound to ZHIE through EDC.

First, 1 mg of ZHIE was shaken at a high speed in 1 ml of methanol in the presence of zirconia particles (particle diameter: 0.8 to 2 mm, 0.5 mg) for 15 minutes to 30 minutes. After the zirconia particles had been removed, the remainder was centrifuged at 2000 rpm for 5 minutes so that a precipitate might be removed. Next, the remainder was subjected to an ultrasonic treatment under the treatment conditions of an oscillatory frequency of 28 kHz, an output of 20 W, 20 or more cycles of "10 to 30 sec ON/10 to 30 sec OFF," and a temperature of 4° C. to 25° C. After that, the solvent was evaporated with a suction aspirator. The evaporation treatment was terminated at such a level that the treated product did not completely exsiccate. Next, 4-(2-hydroxyethyl)-1-piperazineethanesulfonic acid (HEPES: manufactured by Wako Pure Chemical Industries, Ltd.) was added as a buffer solution so that ZHIP might be dispersed well.

Meanwhile, 1 mg of zymosan (β glucan derived from baker's yeast: manufactured by Sigma-Aldrich Corporation) was dispersed in 1 ml of a 2-(N-morpholino)ethanesulfonic acid (MES) buffer solution [0.1 M MES, 0.5 M NaCl, pH 6.0]. After that, 0.4 mg of 1-ethyl-3-[3-dimethylaminopropyl]carbodiimide hydrochloride (EDC: manufactured by Pierce) and 1.2 mg of N-hydroxysulfosuccinimide (sulfo-NHS: manufactured by Pierce) were added to the mixture, and then the whole was subjected to a reaction for 15 minutes at room temperature. The reaction was stopped by adding 2-mercaptoethanol (2-ME: manufactured by Wako Pure Chemical Industries, Ltd.) so that its final concentration might be 20 mM. Then, the resultant was subjected to centrifugal separation at 5000 rpm for 3 minutes so that zymosan might be precipitated. The supernatant was removed, and then 1 ml of an HEPES buffer solution was added to the remainder. The centrifugal separation operation was repeated twice so that 2-ME, and unreacted EDC and sulfo-NHS might be removed, and the buffer solution might be replaced with HEPES. It should be noted that those operations were quickly performed because EDC bound to zymosan was instable.

Figures 1, 20:
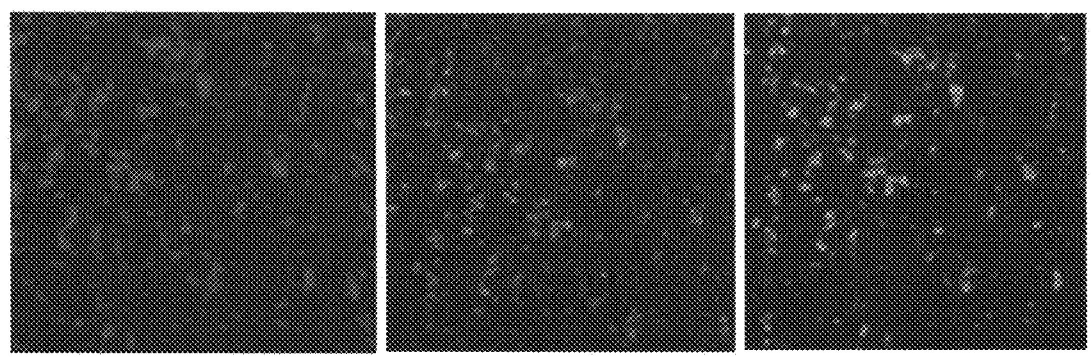
Figures 2, 19:
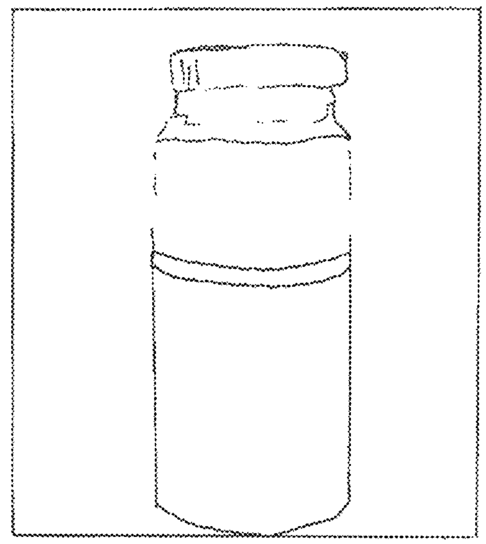
Figures 2, 20:
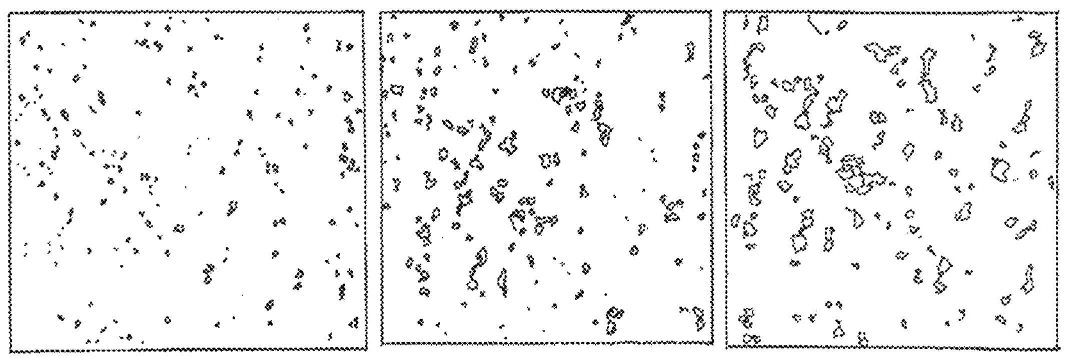

Next, ZHIE dispersed in the HEPES buffer solution was added to zymosan treated with EDC described above, and then the mixture was subjected to a reaction at room temperature for at least two hours while being moderately rotated in a reaction tube. After that, 10 mM of hydroxyamine were added to stop the reaction. The same centrifugation as that described above was performed so that zymosan to which ZHIE was bound might be precipitated. Unbound ZHIE was removed, and the solvent was replaced with a PBS (physiological saline) in a washing step. Thus, the target fluorescent labeling agent (zymosan to which zinc oxide nanoparticles were bound) was obtained. FIG. 20 each show the manner in which fluorescence achieved by irradiating the fluorescent labeling agent with excitation light changed from ultraviolet light to visible light is observed as blue light emission, green light emission, or red light emission through a filter. As is apparent from the figures, the fluorescent labeling agent enables the observation of fluorescence as various luminescent colors. In addition, it was confirmed that the fluorescent labeling agent was stable even after storage in the PBS at 4° C. for one week.

<Example of Fluorescent Labeling: Observation of Phagocytic Action>

Next, an experiment on the observation of the phagocytic action of a mouse macrophage was performed with the above-mentioned fluorescent labeling agent dispersed in a physiological saline.

Mouse macrophage-based cells Raw264.7 (20,000 cells/ml) were cultured in a 10% FBS-containing Dulbecco's modified Eagle's medium (DMEM: manufactured by GIBCO), and then zymosan to which zinc oxide nanoparticles were bound described above was added to the cells. The addition amount was such that the number of molecules of zymosan was ten per cell. After a lapse of 30 minutes to 1 hour, the culture solution was replaced with a PBS. After a lapse of 3 minutes, the PBS was exchanged with a new PBS again. After a lapse of an additional three minutes, the PBS was removed, and then a 4% paraformaldehyde/PBS was added to the remainder so that the cells might be fixed for 15 minutes. The paraformaldehyde/PBS was removed, and then a 50% glycerol/PBS was added to the remainder. Then, the manner of fluorescence was observed.

Figures 1, 21:
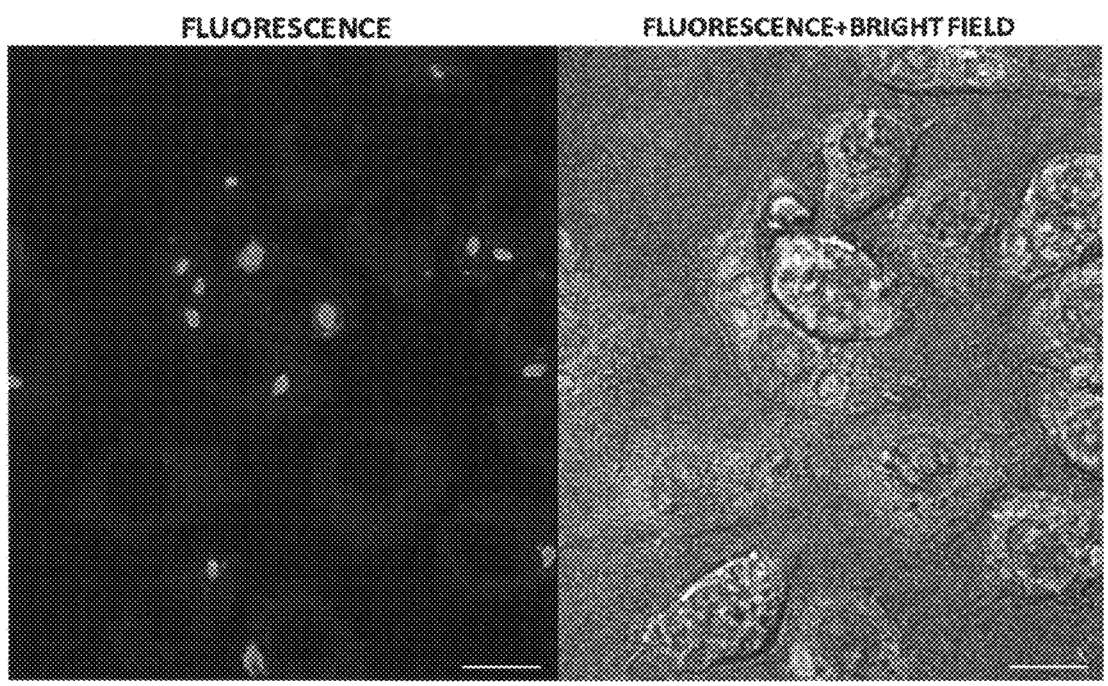

The fluorescence was observed with a fluorescence microscope by using a high-pressure mercury lamp as excitation light. An excitation wavelength ($\lambda_{EX}$) of 360 to 370 nm, a wavelength ($\lambda_{DIC}$) to be separated with a dichroic mirror of 400 nm, and a fluorescence wavelength ($\lambda_{EM}$) of 400 nm or more were observed. FIG. 21 are photographs showing the results of the observation. It was able to be confirmed that a zymosan portion taken up by the phagocytic action of each of the Raw264.7 cells was clearly labeled.

The phagocytic action of an alveolar macrophage was also observed. Specifically, the tail of an alive Balb/c mouse was subjected to intravenous injection with a fluorescent labeling agent (zymosan to which zinc oxide nanoparticles were bound). After a lapse of 30 minutes from the administration, the lung was taken out and sliced. The sliced lung was placed as it was on a slide glass, and then the manner of fluorescence was observed.

Figures 1, 22:
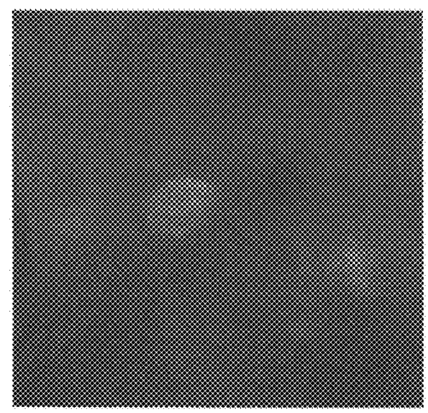
Figures 2, 21:
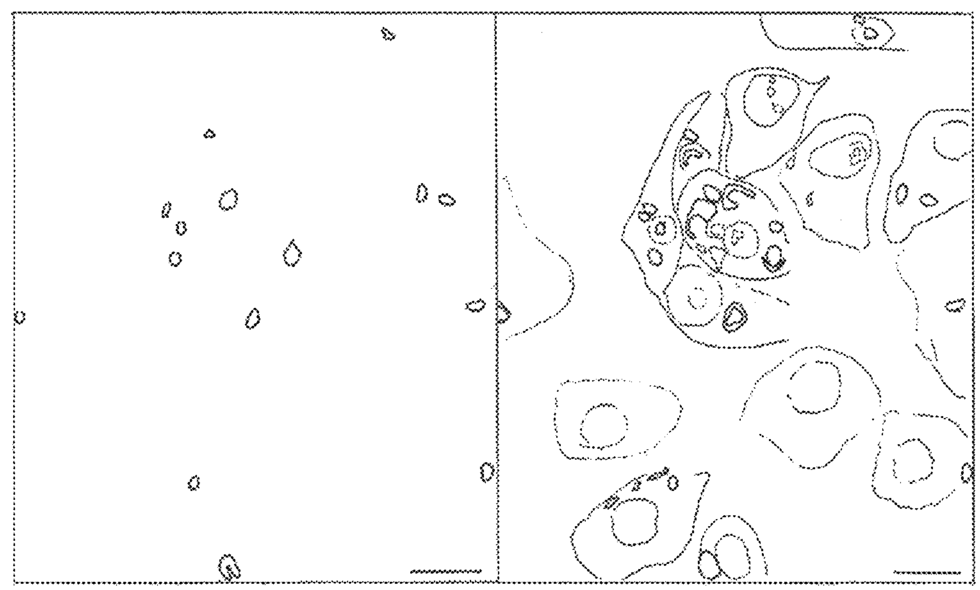
Figures 2, 22:
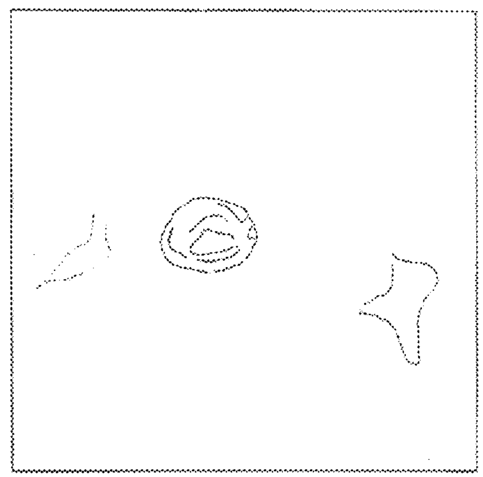

The fluorescence was observed with a fluorescence microscope by using a high-pressure mercury lamp for excitation light. An excitation wavelength ($\lambda_{EX}$) of 360 to 370 nm, a wavelength ($\lambda_{DIC}$) to be separated with a dichroic mirror of 400 nm, and a fluorescence wavelength ($\lambda_{EM}$) of 400 nm or more were observed. FIG. 22 are photographs showing the results of the observation. It was able to be confirmed that a zymosan portion taken up by the phagocytic action of the alveolar macrophage was clearly labeled. The result can be said to demonstrate that the fluorescent labeling agent stably flows in the blood in a living organism and does not lose its fluorescent characteristic.

The zinc oxide nanoparticles of which the fluorescent labeling agent obtained by the above-mentioned production method is constituted are a nontoxic material, show nearly no color deterioration, and as shown in FIGS. 20, 21, and 22, enable dynamic observation of the phagocytic action of a target cell. In addition, the fluorescent labeling agent can similarly label, for example, a cell membrane component derived from *Escherichia coli* as well as zymosan, and hence can find use in researches on phagocytosis and endocytosis.

<Preparation Example 2 of Fluorescent Labeling Agent with ZHIE>

One milligram of ZHIE was subjected to an ultrasonic treatment in methanol in the same manner as that described above so as to be dispersed. Then, the solvent was evaporated with a suction aspirator (provided that the evaporation treatment was terminated at such a level that the treated product did not completely exsiccate).

Meanwhile, 200 mg of an antibody specific to a membrane antigen Mac-1 of the Raw264.7 cells were dissolved in HEPES (40 ml). 0.04 Milligram of EDC and 0.12 mg of NHS were added to the solution, and then the mixture was subjected to a reaction for 15 minutes at room temperature. Immediately after that, 1 ml of HEPES was added to dilute the reaction liquid sufficiently. Then, the diluted solution was injected into a reaction tube containing ZHIE treated as described in the foregoing. The mixture was subjected to a reaction for at least two hours at room temperature while being moderately rotated in the reaction tube. Next, ultrafiltration with a Microcon (molecular cutoff: 3000 MW, manufactured by Millipore) was thoroughly performed so that HEPES might be replaced with a PBS. As a result of the foregoing treatment, the target fluorescent labeling agent (anti-Mac-1 antibody to which zinc oxide nanoparticles were bound) was obtained.

<Example of Fluorescent Labeling: Antibody Labeling>

Figures 2, 23:
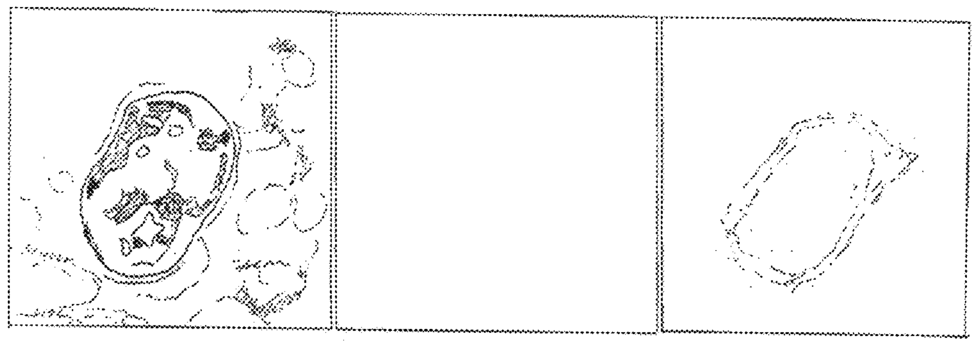
Figures 1, 23:
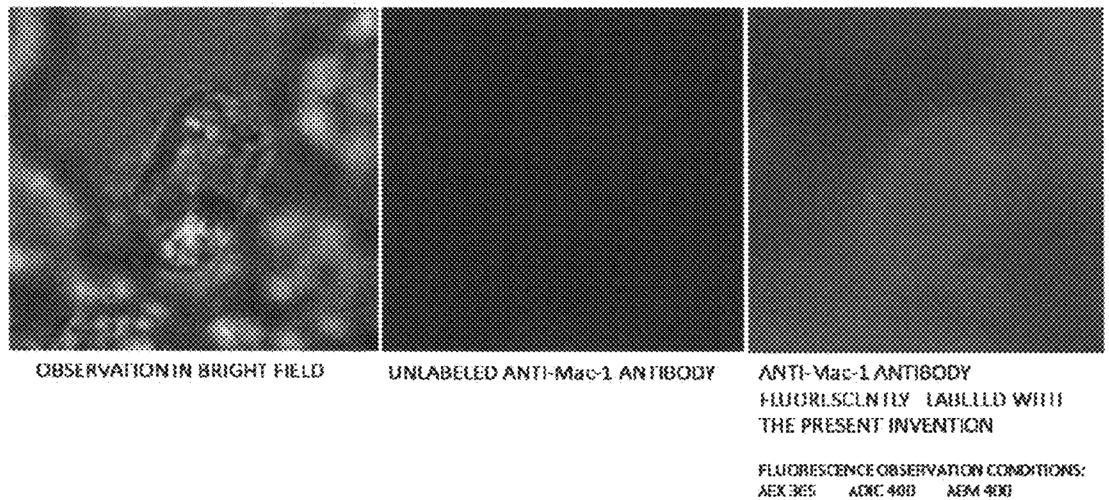

Next, an antibody labeling experiment was performed with the fluorescent labeling agent. First, the anti-Mac-1 antibody to which the zinc oxide nanoparticles were bound was added to a culture solution, and was then caused to react with Raw264.7 cells at 37° C. for 2 hours. The PBS was exchanged with a new PBS. After a lapse of 5 minutes, the PBS was removed, and then a 4% paraformaldehyde/PBS was added to the remainder so that the cells might be fixed for 15 minutes. The paraformaldehyde/PBS was removed, and then the remainder was enclosed with a 50% glycerol/PBS. Then, the manner of fluorescence was observed. Conditions for the observation were identical to those in the case of the phagocytic action. FIG. 23 show the results. As is apparent from the figures, only a specific antibody (Mac-1) that recognized the Raw264.7 cells was able to be caused to emit light.

<Cytotoxicity Test of ZHIE>

Figure 24:
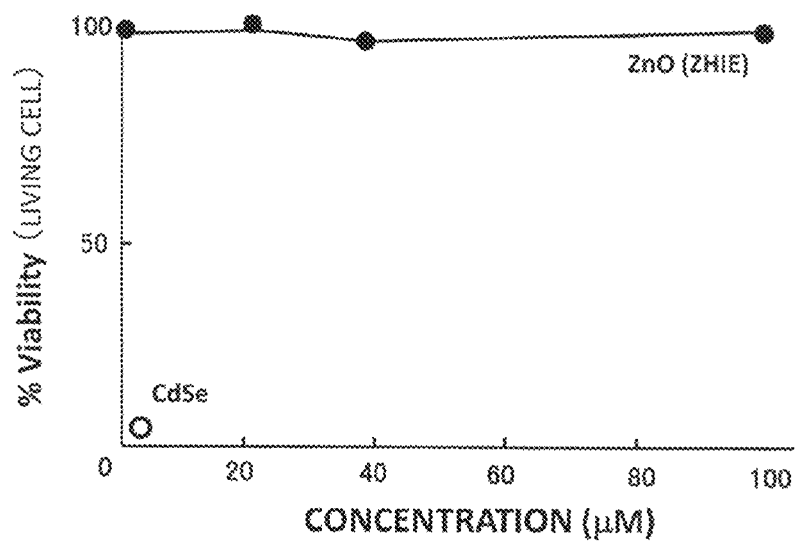
FIG. 24 is a view illustrating the results of the cytotoxicity test of ZHIE.

Next, the cytotoxicity test of the fluorescent labeling material ZHIE of which the fluorescent labeling agent of the present invention was constituted was performed. Under a condition of the number of Raw264.7 cells of 50,000 cells/well, ZHIE was added at various concentrations (0 to 100 mM), and 24 hours after that, whether the cells were dead or alive was measured by a trypan blue method. FIG. 24 illustrates the results of the measurement. It was confirmed that the cells did not die out even at the highest concentration, i.e., 100 mM. In consideration of the fact that there exists a document describing that cadmium selenide (CdSe) as a promising candidate for a fluorescent labeling material that has been studied in recent years shows cytotoxicity at 10 nM, the foregoing results show that the cytotoxicity of ZHIE, even if present, is extremely low as compared with that of CdSe, or specifically 1/10,000 or less of that of CdSe. The cytotoxicity is at such a level that ZHIE can be said to be free of toxicity in practical use. In addition, ZHIE can be said to make various kinds of fluorescent labeling not only in vitro but also in vivo feasible because ZHIE can bind to various antibodies and the like.

Embodiment 2

In Embodiment 2, the case where n in the chemical formula (1) equals 1 is described. The case is such that glycolic acid is used instead of HPA as a raw material. Since glycolic acid is a solid crystal, glycolic acid is easy to handle as compared with HPA, and obviates the need for an operation such as moisture removal with an evaporator. Specifically, an example with a fluorescent labeling material named ZGAI by the inventors of the present invention is described.

Figure 25:
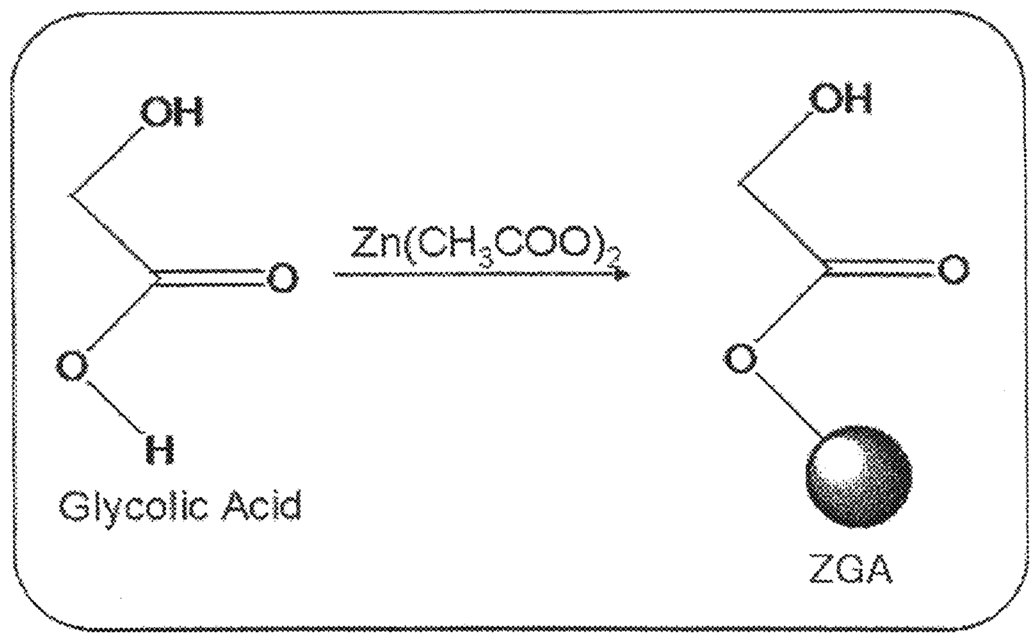
FIG. 25 is a view illustrating a scheme for preparing ZGA with zinc acetate and glycolic acid.
Figure 26:
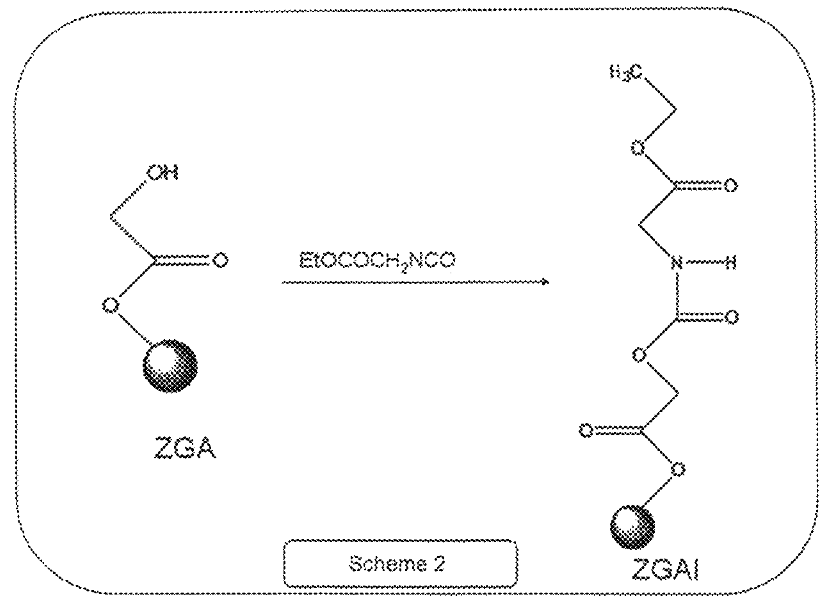
FIG. 26 is a view illustrating a scheme for preparing ZGAI from ZGA.

Only reaction schemes for the preparation of the fluorescent labeling material of Embodiment 2 are described because the preparation is the same as that in Embodiment 1.
(1) Organic matter whose terminals are OH groups is introduced onto the surface of a zinc oxide crystal of several nanometers in size by using zinc acetate monohydrate as a starting material (FIG. 25: preparation of ZGA).
(2) Next, organic matter having an isocyanate group and an ester group is used so that the OH group at the terminal and the isocyanate group may be caused to react with each other (FIG. 26: preparation of ZGAI). As a result, a urethane group as a first auxochrome is introduced.
(3) Next, an amidation reaction is performed with a hydrocarbon compound having amino groups at both terminals so that an amide group as a second auxochrome may be introduced. Thus, zinc oxide nanoparticles having amino groups at their outer ends are prepared (FIG. 27: preparation of ZGAIE).

Figure 27:
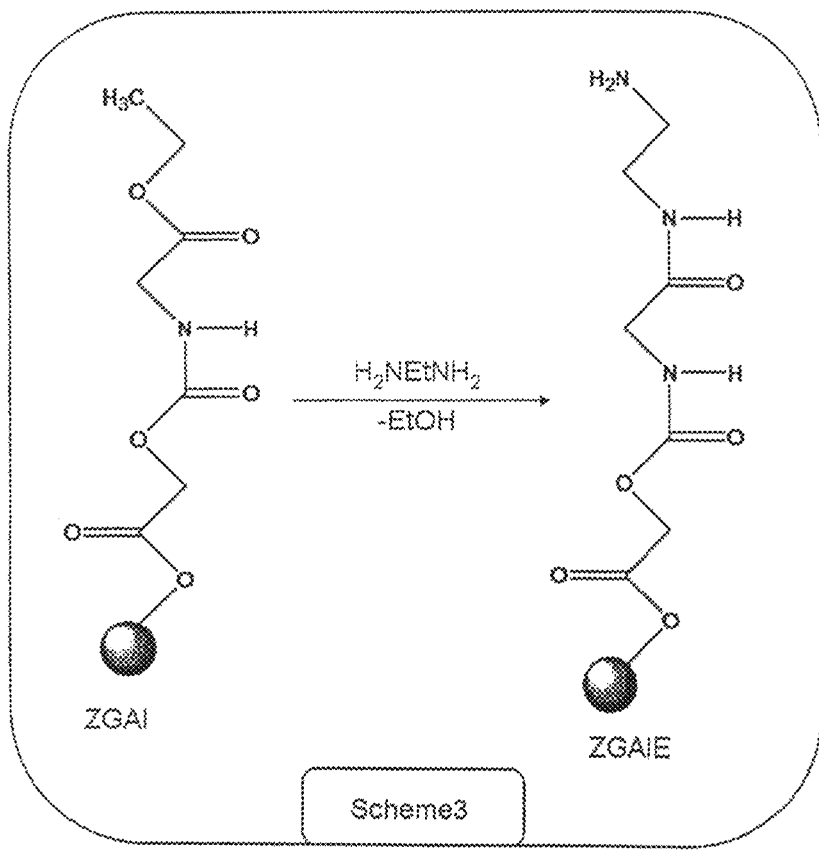
FIG. 27 is a view illustrating a scheme for preparing ZGAIE from ZGAI.
Figure 28:
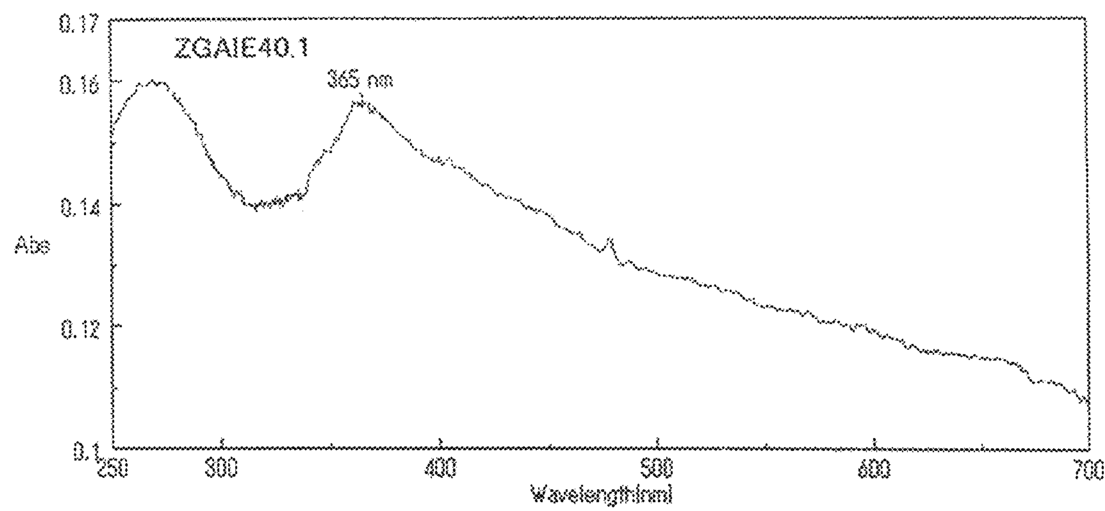
FIG. 28 is a view illustrating the result of the measurement of the absorption spectrum of ZGAIE.
Figure 29:
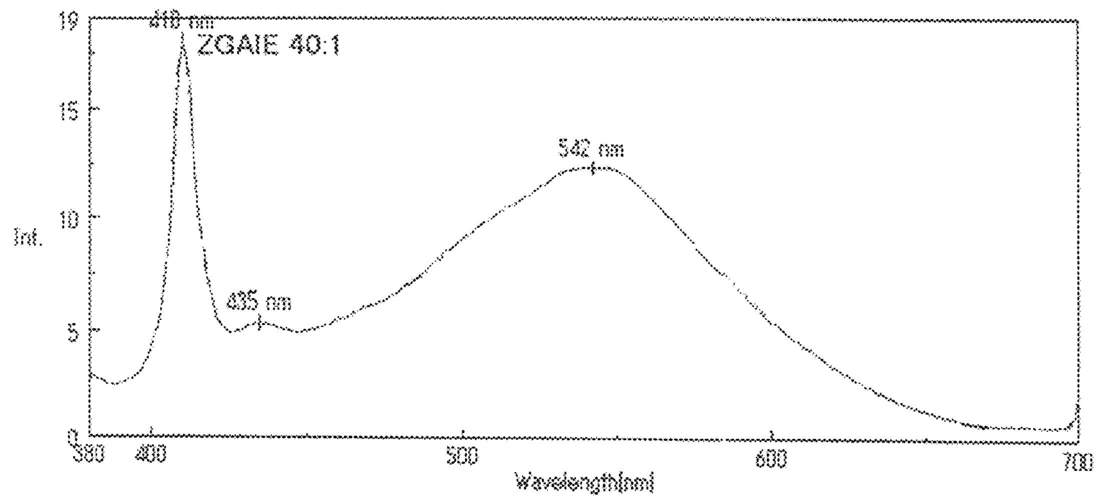
FIG. 29 is a view illustrating the result of the measurement of the fluorescent spectrum of ZGAIE in methanol.
Figure 30:
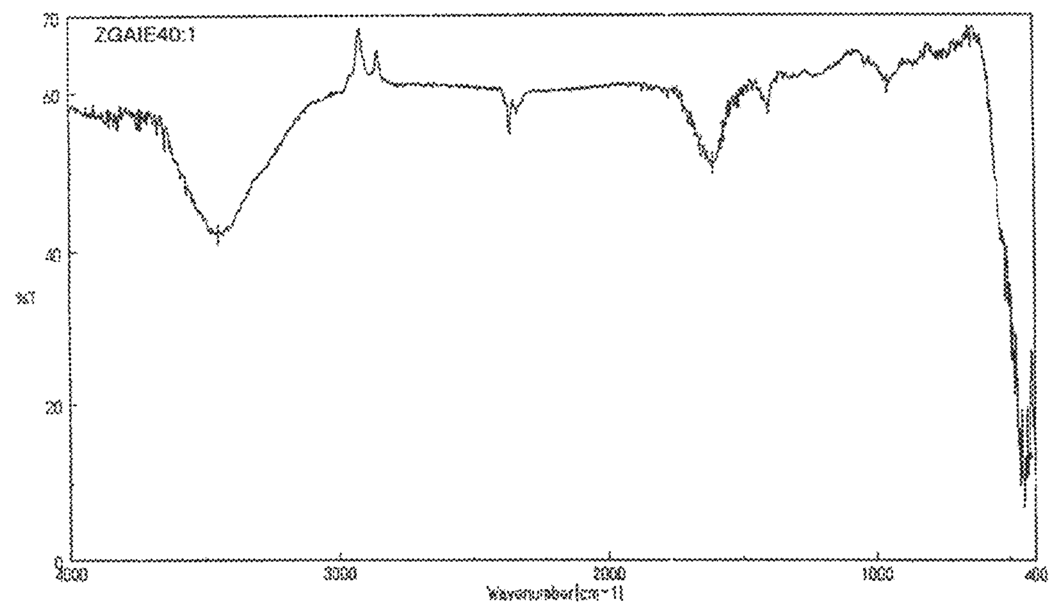
FIG. 30 is a view illustrating the result of the measurement of the FT-IR spectrum of ZGAIE.
Figure 31:
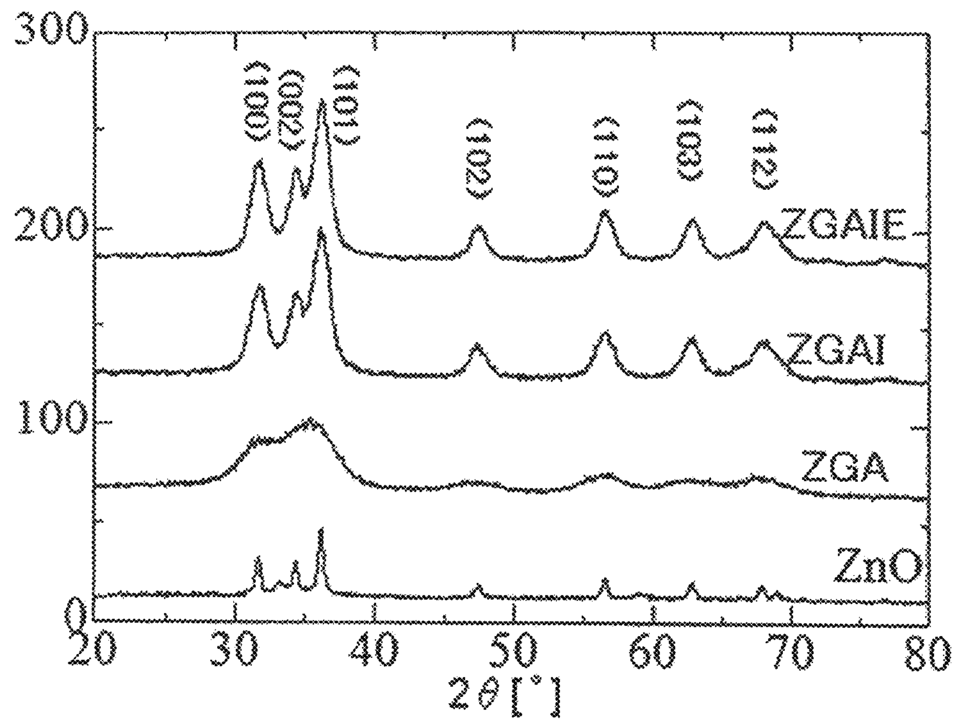
FIG. 31 is a view illustrating the XRD pattern of ZGAIE.

Although FIGS. 25, 26, and 27 each illustrate a substance in such a manner that the surface of the zinc oxide nanoparticle is modified with one molecule of the above-mentioned organic matter having amino groups at the terminals, a large number of molecules of the organic matter are actually bound to the surface so as to form a coating.

It should be noted that it was confirmed that ZGAIE was able to be actually prepared by setting a molar ratio "ZnO: glycolic acid" to 40:1 or 80:1 in accordance with the above-mentioned schemes. Hereinafter, an example in which ZGAIE prepared at a molar ratio of 40:1 was used is described.

Next, the UV spectrum, PL spectrum, FT-IR spectrum, and XRD pattern of ZGAIE thus obtained were measured. FIGS. 28, 29, 30, and 31 illustrate the results of the measurements, respectively. Those results confirmed that the zinc oxide nanocrystal whose surface was modified with the binding chain obtained by setting n in the chemical formula (1) equal to 1 was prepared indeed.

Although the foregoing description relates to the case where n in the chemical formula (1) equals 1, fluorescent labeling materials in which n equals any one of 3, 4, 5, and 6 can be similarly obtained by using 4-hydroxybutyric acid, 5-hydroxyvaleric acid, 6-hydroxyhexanoic acid, and 7-hydroxyheptanoic acid as starting materials, respectively. A desired fluorescent labeling agent can be designed with any such fluorescent labeling material by: binding EDC or the like through the amino group at the terminal of the material; and linking a substance capable of selectively binding to a target to be fluorescently labeled.

INDUSTRIAL APPLICABILITY

As described above, the zinc oxide nanoparticles of which the fluorescent labeling agent of the present invention is constituted can find use in assorted applications because the nanoparticles have the following characteristics. The nanoparticles are a nontoxic material, show nearly no color deterioration, and can fluorescently label a target cell with ease.

In addition to the above-mentioned examples, for example, a fluorescent labeling agent containing a biotin-labeled cancer-specific antibody and streptavidin for recognizing a cancer cell is conceivable. An enhancing effect on fluorescence can be expected from streptavidin because streptavidin has such property as to capture biotin efficiently.

Alternatively, a fluorescent labeling agent prepared by binding ZHIE to a secondary antibody can be used as an indirect fluorescent antibody. That is, when the antibody of a mouse is used as a primary antibody, a fluorescent labeling agent serving as an anti-mouse antibody that emits fluorescence can be used as the secondary antibody. The industrial usefulness of the secondary antibody is imponderable because the secondary antibody has general-purpose property in life science studies and is not fastidious about any antibody species.

With regard to another example of the use of the present invention, the present invention can be used in a diagnosis for specifying a cancer portion during an operation. For example, in an operation for extirpating a bladder cancer, a perioperative diagnosis for making an immediate judgment as to whether an affected area is positive or negative can be performed with a cancer antigen-specific antibody to which zinc oxide nanoparticles are bound by fluorescently labeling the affected area through the application of laser. Alternatively, the present invention can be applied to a wide variety of clinical laboratory tests such as the diagnosis of a skin cancer because of its non-toxicity.

The invention claimed is:

1. A fluorescent labeling material, comprising zinc oxide nanoparticles each surface-modified with an organic compound having an amino group placed at an outer end thereof, wherein the organic compound comprises a binding chain represented by the following formula:

(1)

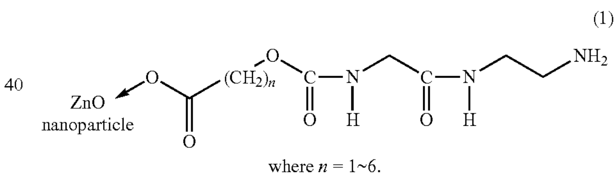

where $n$ = 1~6.

2. A fluorescent labeling material according to claim 1, wherein the fluorescent labeling material has a particle diameter of 15 nm or less.

3. A fluorescent labeling material according to claim 1, wherein the zinc oxide nanoparticles each have crystallinity with which the nanoparticle emits fluorescence.

4. A fluorescent labeling agent to be used in vivo or in vitro, comprising the fluorescent labeling material according to any one of claims 1 to 3, wherein:

3-[(2-aminoethyl)dithio]propionic acid (AEDP), 4-(p-azidosalicylamido)butylamine (ASBA), 1-ethyl-3-[3-dimethylaminopropyl]carbodiimide hydrochloride (EDC), or EDC to which N-hydroxysulfosuccinimide (Sulfo-NHS) is added is bound thereto through the amino group; and a substance capable of selectively binding to a target to be fluorescently labeled is linked thereto.

5. A fluorescent labeling agent according to claim 4, wherein the substance capable of selectively binding to a target is an antibody, an enzyme, a lectin, or a nucleic acid.

6. The fluorescent labeling agent according to claim 4 or 5, wherein the target to be fluorescently labeled comprises:

a tumor cell, a leukemia cell, a virus-infected cell, or a normal cell,
a protein,
an enzyme, or
a nucleic acid.

7. The fluorescent labeling agent according to claim 5, wherein the target to be flourescently labeled comprises: a tumor cell, a leukemia cell, a virus-infected cell, or a normal cell, a protein, an enzyme, or a nucleic acid.

* * * * *